US005559034A

United States Patent [19]
Roberts et al.

[11] Patent Number: 5,559,034
[45] Date of Patent: Sep. 24, 1996

[54] SYNERGISTIC ANTIFUNGAL PROTEIN AND COMPOSITIONS CONTAINING SAME

[75] Inventors: Walden K. Roberts, Denver; Claude P. Selitrennikoff, Evergreen, both of Colo.; Bridget E. Laue, Davis, Calif.; Sharon L. Potter, Raleigh, N.C.

[73] Assignee: Ciba-Geigy Corporation, Tarrytown, N.Y.

[21] Appl. No.: 457,552

[22] Filed: Jun. 1, 1995

Related U.S. Application Data

[60] Division of Ser. No. 178,708, Jan. 10, 1994, which is a continuation-in-part of Ser. No. 505,781, Apr. 6, 1990, abandoned, which is a continuation-in-part of Ser. No. 104,755, Oct. 2, 1987, abandoned.

[51] Int. Cl.$^6$ ............................. C12N 15/00; C12N 1/20; C07H 19/00; C07H 21/00
[52] U.S. Cl. ................. 435/320.1; 435/69.1; 435/252.3; 514/2; 514/8; 514/12; 530/372; 530/376; 536/22.1; 536/23.1; 536/23.6
[58] Field of Search ..................... 514/2, 8, 12; 530/372, 530/376; 435/69.1, 252.3, 320.1; 536/22.1, 23.1, 23.6

[56] References Cited

U.S. PATENT DOCUMENTS 4,486,451  12/1984  Linton et al. ............................ 426/630

FOREIGN PATENT DOCUMENTS

| | | |
|---|---|---|
| 0392255A2 | 3/1990 | European Pat. Off. . |
| 0440304A1 | 1/1991 | European Pat. Off. . |
| 0460753A3 | 5/1991 | European Pat. Off. . |
| 0616035A2 | 10/1993 | European Pat. Off. . |
| 0612847A3 | 2/1994 | European Pat. Off. . |
| WO89/02744 | 4/1989 | WIPO . |
| WO92/20801 | 11/1992 | WIPO . |
| WO93/04586 | 3/1993 | WIPO . |
| WO94/08009 | 4/1994 | WIPO . |

OTHER PUBLICATIONS

European International Search Report dated Dec. 1, 1992.
European International Search Report dated May 29, 1995.
Brogmeyer, J. R., et al., "Isolation and Characterization of 25 kDa Antifungal Protein from Flax Seeds", *Biochemical and Biophysical Research Communications*, 187: 480–487 (1992).
Frendo, P., et al., "Abiotic stresses induce a thaumatin–like protein in maise: cDNA isolation and sequence analysis", *Biological Abstracts*, 94: AB–546 (1992).
Hejgaard, J., et al., "Two antifungal thaumatin–like proteins from barley grain", *FEBS* 10261, 291: 127–131 (1991).
Hejgaard, J., et al., "Antifungal activity of chitin–binding PR–4 type proteins from barley grain and stressed leaf", *FEBS* 11387, 307: 389–392 (1992).
Huynh, Q. K., et al., "Isolation and Characterization of A 22 kDa Protein with Antifungal Properties form Maize Seeds", *Biochemical and Biophysical Research Communiations*, 182: 1–5 (1992).
Leah, R., et al., "Biochemical and Molecular Characterization of Three Barley Seed Proteins with Antifungal Properties", *The Journal of Biological Chemistry*, 266: 1564–1573 (1991).
Logemann, L., et al., "Expression of a Barley Ribosome–Inactivating Protein Leads to Increased Fungal Protection in Transgenic Tobacco Plants", *Biotechnology*,10: 305–308 (1992).
Malehorn, D. E., et al., "Characterization and Expression of an Antifungal Zeamatin–like Protein (Zip) Gene from Zea mays", *Plant Physiol.* , 106: 1471–1481 (1994).
Postein, A. S., et al., "A Novel Pathogen—and Wound–Inducible Tobacco *(Nicotiana tabacum)* Protein with Antifungal Activity", *Plant Physiol.*, 104: 109–118 (1994).
Richardson, M., et al., "A possible function for thaumtin and a TMV–induced protein suggested by homology to a maize inhibitor", *Nature*, 327: 432–434 (1987).
Roberts, W. K., et al.,"Zeamatin, an antifungal protein from maize with membrane–permeabilizing activity", *Journal of General Microbiology*, 136: 1771–1778 (1990).
Sambrook, J., et al., "Generation of Probes Specific for Uncloned Genes by Selective Amplification of Particular Segments of cDNA", *Molecular Cloning*, 2: 14.7–14.8 (1989).
Van Den Elzen, P. J. M., et al., "Virus and fungal resistance: from laboratory to field", *Phil. Trans. R. Soc. Lond. B*, 342: 271–278 (1993).
Vigers, A. J., et al., "A New Family of Plant Antifungal Proteins", *Molecular Plant–Microbe Interations*, 4: 315–323 (1991).
Vigers, A. J., et al., "Thaumatin–like pathogenesis–related proteins are antifungal", *Plant Science*, 83: 155–161 (1992).
Witty, M., "Preprothaumatin II is Processed to Biological Activity in *Solanum Tuberosum*", *Biotechnology Letters*, 12: 131–136 (1990).
Becker et al., *Antimicro. Agents Chemother.*, 23: 926–929 (1983).

(List continued on next page.)

*Primary Examiner*—Robert A. Wax
*Assistant Examiner*—Hyosuk Kim
*Attorney, Agent, or Firm*—Andrea C. Walsh, Ph.D.

[57] ABSTRACT

Novel plant proteins (SAFPs) which synergize the activity of antifungal antibiotics are identified. SAFPs are demonstrated to synergize antifungal antibiotics, such as nikkomycins, polyoxins and amphotericins. SAFPs alone also display antifungal activity against several species of fungi, including strains of Candida, Trichoderma, Neurospora and strains of the plant pathogens Fusarium, Rhizoctonia and Chaetomium. Synergistic antifungal compositions containing SAFP and antifungal antibiotics are provided. In particular, synergistic compositions of corn-SAFP (zeamatin), sorghum-SAFP (sormatin) or oat-SAFP (avematin) and nikkomycin are found to be effective as antifungal compositions, especially against the opportunistic human pathogen *Candida albicans*. Method for employing SAFPs and synergistic compositions containing them for the inhibition of fungi are provided. In addition, a method for purifying SAFP from grain meal is provided.

2 Claims, 10 Drawing Sheets

OTHER PUBLICATIONS

Bhakdi and Tranum–Jensen, *Reviews of Physiology, Biochemistry and Pharmacology*, 107: 147–223 (1984).

Blanco–Labra et al., *J. Food Biochem.*, 5(1): 1–17 (1987).

Blanco–Labra et al., abstract only, *J. Food Biochem.*, 5(1): 1–17 (1981) (in Chem. Abstracts 96: 158/18m, p. 340, 1982).

Bohlmann et al., *EMBO J.*, 7: 1559–1565 (1988).

Bryngelsson and Green, *Physiol. and Mol. Plant Path.*, 35: 45–52 (1989).

Chalkley et al., *Sabouraudia*, 23: 147–164 (1985).

Coleman and Roberts, *Biochim. Biophys. Acta*, 659: 57–66 (1981).

Coleman and Roberts, *Biochim. Biophys. Acta*, 696: 239–244 (1982).

Cornelissen et al., *Nature*, 321: 531–532 (1986).

Data Sheet providing a comparison of the partial sequence of zeamatin with that of MAI as disclosed in Richardson et al., *Nature*, 327: 432–434 (1987).

Davies and Pope, *Nature*, 273: 235–236 (1978).

Edens et al., *Gene*, 18: 1–12 (1982).

Hare and Loebenberg, *ASM News*, 54(5): 235–239 (1988).

Hector and Braun, *Antimicro. Agents Chemother.*, 29: 389–394 (1986).

Hector et cl., *Antimicro. Agents Chemother.*, 34(4): 587–593 (1990).

McCarthy et al., *J. Gen. Microbiol.*, 131: 775–780 (1985).

Mehta et al., *Antimicro. Agents Chemother.*, 25: 373–374 (1984).

Pierpont et al., *Physiol. Mol. Plant Pathol.*, 31: 291–298 (1987).

Pope amd Davies, *Postgraduate Med. J.*, 55: 674–676 (1979).

Roberts et al., *Ann. N.Y. Acad. Sci.*, 544: 141–151 (1988).

Roberts and Selitrennikoff, *Biochem. Biophys. Acta*, 880: 161–170 (1986).

Roberts and Selitrennikoff, *J. Gen. Microbiol.*, 134: 169–176 (1988).

Roberts and Stewart, *Biochemistry*, 12: 2615–2621 (1978).

Selitrennikoff, C. P., *Biotechnology of Filamentous Fungi*, "Screening for Antifungal Drugs", Chapter 8, pp. 189–217 (1992).

Sing et al., *Plant Physiol.*, 85: 529–536 (987).

Van Den Elzen, P. J. M., et al., "Virus and fungal resistance: from laboratory to field", *Phil. Trans. R. Soc. Lond. B*, 342: 271–278 (1993).

Yadan et al., *J. Bacteriol.*, 160: 884–88 (1984).

Yphantes et al., J. Bacteriol., 94: 1509–1515 (1967).

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Peptide
        ( B ) LOCATION: 1..30
        ( D ) OTHER INFORMATION: /note="N-terminal amino acid sequence of Zeamatin"

( x i ) SEQUENCE DESCRIPTION: SEQ ID NO:1:

```
Ala Val Phe Thr Val Val Asn Gln Cys Pro Phe Thr Val Trp Ala Ala
1               5                   10                  15
Ser Val Pro Val Gly Gly Gly Arg Gln Leu Asn Arg Gly Glu
            20              25                  30
```

( 2 ) INFORMATION FOR SEQ ID NO:2:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Peptide
        ( B ) LOCATION: 1..22
        ( D ) OTHER INFORMATION: /note="N-terminal amino acid
            sequence of Sormatin"

( x i ) SEQUENCE DESCRIPTION: SEQ ID NO:2:

```
Ala Val Phe Thr Val Val Asn Arg Cys Pro Tyr Thr Val Trp Ala Ala
1               5                   10                  15
Ser Val Pro Val Gly Gly
            20
```

( 2 ) INFORMATION FOR SEQ ID NO:3:

( i ) SEQUENCE CHARACTERISTICS:
        ( A ) LENGTH: 206 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( i x ) FEATURE:
        ( A ) NAME/KEY: Protein
        ( B ) LOCATION: 1..206
        ( D ) OTHER INFORMATION: /note="Amino acid sequence for
            Zeamatin protein. Mature protein begins at
            residue 21."

( x i ) SEQUENCE DESCRIPTION: SEQ ID NO:3:

```
Ala Val Phe Thr Val Val Asn Gln Cys Pro Phe Thr Val Trp Ala Ala
1               5                   10                  15
Ser Val Pro Val Gly Gly Gly Arg Gln Leu Asn Arg Gly Glu Ser Trp
            20              25                  30
Arg Ile Thr Ala Pro Ala Gly Thr Thr Ala Ala Arg Ile Trp Ala Arg
        35          40                  45
Thr Gly Cys Gln Phe Asp Ala Ser Gly Arg Gly Ser Cys Arg Thr Gly
    50              55                  60
Asp Cys Gly Gly Val Val Gln Cys Thr Gly Tyr Gly Arg Ala Pro Asn
65              70                  75                  80
```

```
Thr Leu Ala Glu Tyr Ala Leu Lys Gln Phe Asn Asn Leu Asp Phe Phe
                85                      90                      95

Asp Ile Ser Ile Leu Asp Gly Phe Asn Val Pro Tyr Ser Phe Leu Pro
            100                 105                 110

Asp Gly Gly Ser Gly Cys Ser Arg Gly Pro Arg Cys Ala Val Asp Val
        115             120                 125

Asn Ala Arg Cys Pro Ala Glu Leu Arg Gln Asp Gly Val Cys Asn Asn
    130                 135                 140

Ala Cys Pro Val Phe Lys Lys Asp Glu Tyr Cys Cys Val Gly Ser Ala
145                 150                 155                 160

Ala Asn Asn Cys His Pro Thr Asn Tyr Ser Arg Tyr Phe Lys Gly Gln
                165                 170                 175

Cys Pro Asp Ala Tyr Ser Tyr Pro Lys Asp Asp Ala Thr Ser Thr Phe
            180                 185                 190

Thr Cys Pro Ala Gly Thr Asn Tyr Lys Val Val Phe Cys Pro
            195                 200                 205
```

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Degenerate nucleotide SP86 based on
            amino acid sequence of zeamatin ( i i i ) HYPOTHETICAL: NO ( i v ) ANTI-SENSE: NO ( i x ) FEATURE:
        ( A ) NAME/KEY: modified_base
        ( B ) LOCATION: 13
        ( D ) OTHER INFORMATION: /mod_base=i ( i x ) FEATURE:
        ( A ) NAME/KEY: modified_base
        ( B ) LOCATION: 16
        ( D ) OTHER INFORMATION: /mod_base=i ( i x ) FEATURE:
        ( A ) NAME/KEY: modified_base
        ( B ) LOCATION: 19
        ( D ) OTHER INFORMATION: /mod_base=i ( x i ) SEQUENCE DESCRIPTION: SEQ ID NO:4:

```
ATGTGAATTC GGNCANAANA CYTTRTARTT                                         30
```

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Degenerate nucleotide SP87 based on
            amino acid sequence of zeamatin ( i i i ) HYPOTHETICAL: NO ( i v ) ANTI-SENSE: NO ( i x ) FEATURE:
        ( A ) NAME/KEY: modified_base
        ( B ) LOCATION: 12

( D ) OTHER INFORMATION: /mod_base=i ( i x ) FEATURE:
    ( A ) NAME/KEY: modified_base
    ( B ) LOCATION: 15
    ( D ) OTHER INFORMATION: /mod_base=i ( i x ) FEATURE:
    ( A ) NAME/KEY: modified_base
    ( B ) LOCATION: 21
    ( D ) OTHER INFORMATION: /mod_base=i ( i x ) FEATURE:
    ( A ) NAME/KEY: modified_base
    ( B ) LOCATION: 30
    ( D ) OTHER INFORMATION: /mod_base=i ( x i ) SEQUENCE DESCRIPTION: SEQ ID NO:5:

ATGTGAATTC ANCANTAYTC NTCYTTYTTN AA    32

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Degenerate nucleotide SP88 based on
            amino acid sequence of zeamatin ( i i i ) HYPOTHETICAL: NO ( i v ) ANTI-SENSE: NO ( i x ) FEATURE:
        ( A ) NAME/KEY: modified_base
        ( B ) LOCATION: 16
        ( D ) OTHER INFORMATION: /mod_base=i ( i x ) FEATURE:
        ( A ) NAME/KEY: modified_base
        ( B ) LOCATION: 22
        ( D ) OTHER INFORMATION: /mod_base=i ( i x ) FEATURE:
        ( A ) NAME/KEY: modified_base
        ( B ) LOCATION: 28
        ( D ) OTHER INFORMATION: /mod_base=i ( i x ) FEATURE:
        ( A ) NAME/KEY: modified_base
        ( B ) LOCATION: 31
        ( D ) OTHER INFORMATION: /mod_base=i ( x i ) SEQUENCE DESCRIPTION: SEQ ID NO:6:

GTACGGATCC AAYCANTGYC CNTTYACNGT NTGG    34

( 2 ) INFORMATION FOR SEQ ID NO:7:

( i ) SEQUENCE CHARACTERISTICS:
        ( A ) LENGTH: 894 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_feature
        ( B ) LOCATION: 19..21

(D) OTHER INFORMATION: /note="Start codon for coding sequence of Zeamatin"

(ix) FEATURE:
(A) NAME/KEY: misc_feature
(B) LOCATION: 82..84
(D) OTHER INFORMATION: /note="First codon of the mature peptide for Zeamatin"

(xi) SEQUENCE DESCRIPTION: SEQ ID NO:7:

| | | | | | | |
|---|---|---|---|---|---|---|
| TTCAAATACT | TGCATAAGAT | GGCAGGTTCC | GTGGCAATCG | TGGGCATCTT | CGTCGCCCTC | 60 |
| CTCGCCGTGG | CCGGCGAGGC | GGCTGTGTTC | ACGGTGGTGA | ACCAGTGCCC | GTTCACCGTG | 120 |
| TGGGCCGCGT | CCGTGCCGGT | GGGCGGCGGG | CGGCAGCTGA | ACCGCGGCGA | GAGCTGGCGG | 180 |
| ATCACGGCCC | CCGCGGGCAC | GACGGCCGCG | CGCATCTGGG | CGCGCACGGG | GTGCAAGTTC | 240 |
| GACGCGAGCG | GGCGCGGGAG | CTGCCGCACG | GGGGACTGCG | GCGGCGTGCT | GCAGTGCACT | 300 |
| GGGTACGGGC | GCGCGCCCAA | CACGCTGGCG | GAGTACGCTC | TGAAGCAGTT | CACAACCTCG | 360 |
| ACTTCTTCGA | CATCTCCCTC | ATCGACGGCT | TCAACGTGCC | CATGAGCTTC | CTCCCCGACG | 420 |
| GCGGGTCCGG | GTGCAACCGC | GGCCCGCGCT | GCGCCGTGGA | CGTGAACGCG | CGCTGCCCTG | 480 |
| CCGAGCTGCG | GCAGGACGGC | GTGTGCAACA | ACGCGTGCCC | CGTGTTCAAG | AAGGACGAGT | 540 |
| ACTGCTGCGT | CGGCTCGGCG | GCCAACGACT | GCCACCCGAC | CAACTACTCC | AGGTACTTCA | 600 |
| AGGGCAGTG | CCCCGACGCG | TACAGCTACC | CCAAGGATGA | CGCCACCAGC | ACCTTCACCT | 660 |
| GCCCCGCCGG | AACCAACTAC | AAGGTCGTCT | TCTGCCCGTG | AGGCCGCTGA | ACTAGCATCA | 720 |
| GCGTGCGCGC | GTCGACCAAG | AACAAGAAAT | AAACGACCGA | GGCTGTGTAT | GTTGCCCGCC | 780 |
| GTGTGCTCAA | CTGGAGCAAA | AATAAAGCCA | ACAAAACAAG | CACGTGTGAT | CTCTATGTCA | 840 |
| CCAACTCTAT | CACCTTAATT | AATGGGGCAT | TATGAAAAAA | AAAAAAAAAA | AAAA | 894 |

SYNERGISTIC ANTIFUNGAL PROTEIN AND COMPOSITIONS CONTAINING SAME

This invention was made with partial government support under contract number DCB 8500233 awarded by the National Science Foundation. The government has certain rights in this invention.

This is a divisional application of Ser. No. 08/178,708, filed Jan. 10, 1994, which is a continuation-in-part of Ser. No. 07/505,781, filed Apr. 6, 1990, now abandoned which is a continuation-in-part of Ser. No. 07/104,755, filed Oct. 2, 1987, now abandoned.

FIELD OF THE INVENTION

This invention relates to novel antifungal plant proteins which synergize and enhance the activity of antifungal antibiotics which are designated synergistic antifungal proteins (SAFPs), particularly those isolated from grains, and especially that isolated from corn (zeamatin). SAFPs alone are useful for the inhibition of growth of certain fungi. The synergistic antifungal compositions of the present invention are generally useful in vitro and in vivo for inhibition of fungal growth and for combatting fungal infections. Zeamatin/nikkomycin compositions are particularly useful in inhibiting the growth of the opportunities human pathogen *Candida albicans* and for combatting candidal infections. Furthermore, the invention relates to genes for novel antifungal proteins and their use in transgenic technologies.

BACKGROUND OF THE INVENTION

There is significant need for effective antimycotic drugs especially for the treatment of systemic fungal infections which are life-threatening, common complications in immune-compromised patients, see for example Hart et al. (1969) J. Infect. Dis. 120:169–191. Among the most virulent organisms are strains of the yeast Candida, most particularly strains of *C. albicans*. While there are several effective topical agents for treatment of candidiases, treatment of systemic infection is much more difficult. The drug of choice for systemic infection is amphotericin B, however this drug is highly toxic to the host (see, for example, Medoff and Kobayashi (1980) New Eng. J. Med. 302:145–55). Antimycotic agents that are more effective and/or less toxic than existing drugs are highly desirable.

Several classes of nucleoside antibiotics, including polyoxins (Hori et al. (1971) Agr. Biol. Chem. 35:1280; Hori et al. (1974) Agr. Biol. Chem. 38:699; Sasaki et al. (1968) Ann. Phytopathol. Soc. Japan 34:272) and nikkomycins (Dahn et al. U.S. Pat. No. 4,046,881 and 4,158,608; Zahner et al. U.S. Pat. No. 4,287,186; Hagenmaier et al. U.S. Pat. No. 4,315, 922) have been reported. Polyoxins and nikkomycins are reported to be useful in agriculture against phytopathogenic fungi and insect pests. Early reports indicated that polyoxins were not effective against zoopathogenic fungi, such as *C. albicans* (see, for example, Gooday (1977) J. Gen. Microbiol. 99:1; Shenbagamurthi et al. (1983) J. Med. Chem. 26:1518–1522). It was believed that the polyoxins were not taken up by target cells. More recently, polyoxins have been reported to inhibit the growth in vitro of certain zoopathogenic fungi including *C. albicans* and *Cryptoccus neoformans* when provided at millimolar concentrations (Becker et al. Antimicro. Agents Chemother. (1983) 23:926–929 and Mehta et al. (1984) Antimicro. Agents Chemother. 25:373–374). Nikkomycins X and Z have now also been reported to inhibit growth of *C. albicans* in vitro (Yadan et al. (1984) J. Bacteriol. 160:884–888; McCarthy et al. (1985) J. Gen. Microbiol. 131:775–780). Polyoxins and nikkomycins are similar in structure and apparently both act as competitive inhibitors of chitin synthetase (Endo et al. (1970) J. Bacteriol. 104:189–196; Muller et al. (1981) Arch. Microbiol. 130:195–197). Chitin is an essential component of the cell wall of most fungi. Nikkomycins appear, however, to be more effective (about 100 fold) against certain fungi, for example *C. albicans*, than polyoxins which is in part due to a higher affinity of nikkomycin for chitin synthetase and more rapid uptake of nikkomycin by *C. albicans* cells (McCarthy et al. (1985) supra). The activity of polyoxins and nikkomycins is reported to be inhibited by peptides, such as those present in rich media (Becker et al., 1983, supra; McCarthy et al., 1985, supra; Mehta et al., 1984, supra). Peptides are believed to inhibit uptake of the antibiotic by target cells. The usefulness of nikkomycins and polyoxins for clinical applications such as in the treatment of systemic fungal infection, where peptide inhibition is likely, is expected to be limited as the concentrations of antibiotic required for effective fungal inhibition are not likely to be achieved in vivo.

Mixtures of antimicrobial agents, particularly mixtures in which the components have different modes of action have been used in antimicrobial compositions to broaden activity spectrum or to minimize the occurrence of resistant strains. Further, certain of these mixtures can display an enhanced antimicrobial activity, greater than the additive activity of the individual components, due to synergy. For example, Gisi et al. (1985) Trans. Br. Mycol. Soc. 85:299–306 reported that a number of fungicide mixtures displayed synergistic activity against phytopathogenic fungi in field tests. The maximum synergy ratio reported was 7, that is a 7-fold enhancement of activity over the calculated additive effect. Fungicide mixtures can also show antagonism with reduced activity of the combination compared to the individual components. It has recently been reported (Hector and Braun (1986) Antimicro. Agent Chemother. 29:389–394) that mixtures of either nikkomycin Z or nikkomycin X with papulacandin B, an inhibitor of β-glucan synthesis, display synergistic antifungal activity against *Candida albicans*. Activity enhancements up to about 10 were reported.

Certain enzymes have also been reported to synergize the effect of antifungal agents. Lysozyme has been reported to synergize the activity of amphotericin B against *Candida albicans* and *Coccidioides immitis* (Collins and Pappagianis (1974) Sabouraudia 12:329–340). Natural mixtures of mycolytic enzymes of fungal origin, designated mycolases, were reported to have a synergistic effect on the activity of the antifungal drugs amphotericin B and nystatin (Davies and Pope (1978) Nature 273:235–6; Pope and Davies (1979) Postgraduate Med. J. 55:674–676). The in vitro MICs (minimum inhibitory concentrations) of these antifungal drugs were lowered about 5 to 10-fold in combinations with mycolase. In related in vivo experiments in a mouse model, fungal mycolase was reported to enhance the effectiveness of amphotericin B and nystatin against systemic infection of *C. albicans*. It was suggested that mycolase, which was suggested to be a mixture of carbohydrases, enhanced penetration of the antibiotic into fungal cells. Fungal mycolases, alone, were described as very effective at releasing protoplasts from *Aspergillus fumigatus* and *C. albicans* in vitro and were also reported to have some effect, alone, against systemic fungal infection in the mouse model system. In contrast, a prepared mixture of the carbohydrases chitinase (β-1,4 N-acetyl-D-glucosaminidase) and laminarinase (β-1, 3(4)-glucanase), while reported to effect protoplast release from *A. fumigatus* and *C. albicans*, did not enhance the effectiveness of amphotericin B and nystatin in vivo. Recently, in similar in vitro and in vivo experiments with fungal mycolase/amphotericin B mixtures, only slight enhancement of antifungal activity by a fungal mycolase was reported (Chalkley et al. (1985) Sabouraudia 23:147–164). This report suggests that the difference in results compared to those reported earlier by Davies and Pope (supra) may be associated with the lower chitinase or lower β-1,6-D-glucanase activities in their preparation of mycolase compared to that employed in the previous experiments. The specific enzymatic activities present in fungal mycolases have not been identified, and the specific protein or proteins in mycolase that may effect antibiotic enhancement have not been identified. Some bacterial mycolases have also been reported to effect enhancements (about 2-fold) of the activity of amphotericin B (Oranusi and Trinci (1985) Microbios 43:17–30). Again, no specific enzyme activity was associated with synergy.

Plants appear to have a variety of mechanisms for protecting themselves against infection by viruses, bacteria, fungi and insects. These mechanisms are believed to include the presence of inhibitory substances in plant tissue or plant excretions. Such inhibitory substances may be present constitutively in the plant or induced by infection and may be low molecular weight compounds such as inhibitins or phytoalexins or certain proteins, for example, peroxidases, proteinase inhibitors, chitinases or β-1,3-glucanases. In most cases, the inhibitory function of these substances have not been demonstrated.

In addition to the specific need for more effective, clinically useful antifungal agents, there is a general need for effective, natural, biodegradable antifungal agents, particularly for use in agriculture against plant pathogenic fungi. Such natural antifungal agents may be considered to be ecologically preferable to chemical fungicides. To be economically useful, especially in agricultural applications, such natural antifungal agents should be available in large amounts from inexpensive sources.

It has been recently reported, Roberts and Selitrennikoff (1986) Biochem. Biophys. Acta 880:161–170, that a class of plant proteins called ribosome-inactivating proteins (RIPs) are effective against certain fungi, for example, *Trichoderma reesei*. These proteins were earlier shown to inhibit protein synthesis in animal cell-free extracts (Coleman and Roberts (1982) Biochem. Biophys. Acta 696:239–244). RIPs isolated from grains, including wheat, barley, rye and corn, reportedly act by enzymatically inactivating the 60S subunit of the animal cell ribosome. Coleman and Roberts (1982) reported that RIPs could be purified to near homogeneity from rye, barley, corn and tritin using the same procedure (roberts and Stewart (1979) Biochemistry 18:2615–2621 ). RIPs from rye, barley and tritin were reported to have apparent molecular weights of approximately 30 kd when analyzed by SDS-PAGE run under reducing conditions, and corn RIP was reported to run as an approximately 23 kd protein under similar conditions. Roberts and Selitrennikoff (1986) supra demonstrated that RIP isolated from barley inactivated Neurospora ribosomes as measured by in vitro inhibition of poly(U)-directed polyphenylalanine synthesis in cytoplasmic ribosome preparations (see also Coleman and Roberts (1981) Biochim. Biophys. Acta 659:57–66). These authors have also reported the presence in barley, corn, wheat and rye of another class of antifungal proteins, designated AFPs which inhibit growth of some fungi, including *T. reesei*, in vitro. The present work is an extension of this work with plant antifungal proteins.

SUMMARY OF THE INVENTION

The present invention is based on the surprising finding that a newly identified class of plant proteins, designated synergizing antifungal proteins or SAFPs, not only have antifungal activity themselves, but also significantly enhance the activity of antifungal agents which are inhibitory to the synthesis of fungal cell walls, including polyoxins, nikkomycins and amphotericins. SAFPs can be isolated from grains or germinating grains, including wheat, rye, barley, sorghum, oats and corn. SAFP activity has also been detected in other plant seeds, such as soybean. The level of SAFP is enhanced in germinating grains, particularly wheat and rye. Corn is particularly preferred as a source of SAFP because active corn-SAFP, herein designated zeamatin, is readily isolated in partially purified or substantially pure form and in relatively large amounts. Corn steepwater, for example, was found to be a source of active zeamatin. Furthermore, corn protein extracts containing corn-SAFP activity were found to be more stable than similar preparations of rye, wheat or barley, which facilitated isolation and purification of SAFP from corn. Also preferred is sorghum-SAFP, herein designated sormatin. This antifungal protein, like zeamatin, retains SAFP activity following extraction and isolation in partially purified or substantially pure form. Also preferred is partially purified oat-SAFP, herein designated avematin. This antifungal protein also retains SAFP activity following extraction and isolation in partially purified form.

SAFP is itself inhibitory to fungi (including strains of Neurospora, Trichoderma, Phycomyces and Alternaria sp.), yeasts (including strains of Candida and Rhodotorula), and plant pathogenic fungi (including strains of Rhizoctonia, Chaetomium and Fusarium), and particularly *Neurospora crassa* and *Trichoderma reesei*. SAFP is in particular inhibitory to the growth of *N. crassa*, *T. reesei* and *C. albicans*, as well as to *Fusarium monoliforme*, *F. proliferatum* and *F. sacchari*.

Antifungal activity of SAFP against Neurospora, Trichoderma, Rhizoctonia, Fusarium and Chaetomium has been assessed in in vitro agar plate assays. In similar plate assays, SAFP showed no growth inhibition of yeasts, including strains of Candida, Rhodotorula and Saccharomyces. However, inhibition assays performed in liquid medium demonstrated that SAFP itself also inhibited the growth of yeasts, particularly *C. albicans*. The synergizing activity of SAFP has been assessed in in vitro assays, for example, as the enhancement of the antifungal activity of nikkomycin Z or nikkomycin X against the opportunistic human pathogen *C. albicans*.

Zeamatin is an approximately 22 kd protein, as assessed in SDS-PAGE electrophoresis under reducing conditions. Under nonreducing conditions, zeamatin migrates at 19 kd. The difference in migration rates is believed to result from the reduction, under reducing conditions, of zeamatin's disulfide bonds to produce a less compact conformation. Zeamatin, in substantially pure form or in partially pure form, displays, in particular, synergistic anti-Candida activity and anti-Neurospora activity; and displays antifungal activity against strains of Trichoderma, Candida, Fusarium, Rhizoctonia and Chaetomium. In particular, corn steepwater and protein concentrates thereof, which contain active zeamatin as evidenced by the distinct protein band at 19 kd (under nonreducing conditions) and by the presence of synergistic anti-Candida activity, are also found to be inhibitory to the growth of fungi, including Trichoderma, Candida, Neurospora and the plant pathogens Fusarium, Rhizoctonia and Chaetomium.

Zeamatin has been isolated in substantially pure form by methods described herein, as demonstrated by the absence of contaminating protein bands in conventional protein gel electrophoresis, as shown in FIG. 4. The N-terminal amino acid sequence (30 amino acids) of zeamatin is provided in Table 5 (SEQ. ID NO: 1). Substantially pure zeamatin displays no detectable chitinase activity, 1-3 β-glucanase, protease, ribonuclease, phospholipase C, mannanase, N-β-acetylhexosaminidase or ribosome-inactivating protein activity as assessed by procedures described herein or well known in the art. Substantially pure zeamatin preparations include those in which the 22 kd protein represents about 90% or more of the total protein present in the preparation. In in vitro synergy plate assays, zeamatin was found to greatly enhance the anti-Candida activity of nikkomycin X or Z up to about 100 fold, while in liquid culture assays, enhancements of up to 1000 fold were observed. Greater enhancement of anti-Candida activity of nikkomycin X or Z is observed in agar-free medium containing low concentrations of peptone and peptides. Zeamatin also displayed significant enhancement (about 10-fold) of the activity of polyoxin against $C.$ $albicans$ and also enhanced (about 3-fold) the activity of amphotericin B against this yeast Sormatin has been isolated in substantially pure form by methods described herein. Sormatin is an approximately 25 kd protein, as assessed in SDS polyacrylamide gel electrophoresis under reducing conditions. The N-terminal partial amino acid sequence of sormatin is given in Table 5 (SEQ. ID NO: 2). Sormatin in substantially pure or partially pure form, displays synergistic anti-Candida activity and also displays antifungal activity against certain strains. Substantially pure sormatin preparations include those in which the 25 kd protein represents about 70–80% or more of the total protein present in the preparation. Avematin has been isolated in partially purified form by methods described herein. Avematin is an approximately 22 kd protein, as assessed in SDS polyacrylamide gel electrophoresis under reducing conditions. Avematin displays synergistic anti-Candida activity and displays antifungal activity against certain strains.

The present invention discloses a novel class of plant proteins, SAFPs, found in grains such as corn, wheat, barley, sorghum, oats and rye, which, in addition to having antifungal activity, enhance the antifungal activity of antimycotics, particularly those which inhibit the synthesis of fungal cell walls. In a specific embodiment, the present invention provides SAFP isolated from corn, zeamatin, in substantially pure form, having synergistic antifungal activity and antifungal activity. The invention also provides partially purified zeamatin preparations having both synergistic antifungal activity and antifungal activity. In another specific embodiment, SAFP isolated from sorghum, sormatin, is provided in substantially pure form, having synergistic antifungal activity and antifungal activity. Also provided are partially purified sormatin preparations having both synergistic antifungal activity and antifungal activity. In another specific embodiment, SAFP isolated from oats, avematin, is provided in partially purified form, having synergistic antifungal activity and antifungal activity.

SAFP can be employed as an antifungal agent against strains of fungi including, among others, Neurospora, Trichoderma, Candida, Fusarium, Rhizoctonia and Chaetomium. Fungal growth inhibition can be accomplished by applying SAFP, in substantially pure form, in partially pure form, or in crude extracts, to a fungal habitat The amount of SAFP that is applied is such that its concentration in the fungal habitat is effective for growth inhibition of that fungus. The mount of a SAFP required for fungal growth inhibition depends on the desired application. The amount of SAFP required for use against a particular fungus in a particular habitat can be readily determined employing appropriate in vitro or in vivo assays that are well known in the art, such as those described herein. For example, it was found that the minimum amount of substantially pure zeamatin required for inhibition of $Neurospora$ $crassa$ in in vitro hyphal extension inhibition assays was about 0.3 g protein/disc. In a similar assay it was found that the minimum mount of substantially pure zeamatin required to inhibit $Trichoderma$ $reesei$ was about 3 g protein/disc. In liquid medium, it was found that between about 10 to 30 g/ml of substantially pure zeamatin was required to inhibit $Canada$ $albicans$. SAFP can in general be employed in any fungal habitat in which is retains antifungal activity. Sormatin, avematin and other grain SAFP's are effective for fungal growth inhibition at levels comparable to those of zeamatin demonstrated to be effective.

The present invention further provides antifungal compositions which contain SAFP in combination with an antifungal antibiotic. SAFP being present in such compositions at a level sufficient to synergize or enhance the antifungal effect of the antibiotic. The antibiotic being present at a sufficient level that the composition has antifungal activity, i.e. inhibits fungal growth. Synergistic compositions are those in which the MIC of the antibiotic in the composition is lower than the MIC of the antibiotic in the absence of SAFP. The antifungal compositions of the present invention preferably contain zeamatin, sormatin or oat-SAFP. More preferably are those containing zeamatin and sormatin, and most preferably zeamatin. While, in principle, any antifungal agent particularly those that inhibit fungal wall synthesis such as amphotericin B, polyoxin and nikkomycin are useful in the compositions of the present invention, compositions containing nikkomycins are preferred. Compositions containing nikkomycin X or nikkomycin Z are more preferred and compositions containing nikkomycin X or nikkomycin Z in combination with zeamatin or sormatin are most preferred.

The amount of an SAFP and a particular antifungal antibiotic that in combination produce a synergistic antifungal composition will vary dependent upon the desired application of the composition. The amounts of SAFP and antibiotic required in a particular application against a particular fungus can be readily determined employing appropriate in vitro or in vivo assays that are well known to the art such as those described herein. For example, it was found that compositions containing about 50 g/ml partially purified matin (fraction CMS) and about 0.06 g/ml nikkomycin displayed synergistic antifungal activity, particularly against $C.$ $albicans$ in plate diffusion disk assays (Table 4). It was found that concentrations of partially purified zeamatin (fraction CMS) of at least about 10 g/ml in combination with about 0.8 g/ml nikkomycin retained antifungal activity against $Candida$ $albicans$ as measured in plate diffusion disc assays. It was found that concentrations of substantially pure zeamatin of about 0.3 g protein/disc or greater, in combination with concentrations of nikkomycin of about 0.2 g/ml or greater inhibited growth of $C.$ $albicans$ in diffusion disc assays. It was further demonstrated that concentrations of substantially pure zeamatin fractions of about 0.3 g protein/ml or greater, in combination with concentrations of nikkomycin of about 0.17 g/ml or greater, inhibited growth of $C.$ $albicans$ in liquid medium.

The synergistic compositions of the present invention are useful in general, as antifungal agents effective against a variety of fungi including both phytopathogenic and zoopathogenic fungi. These synergistic compositions are particularly useful against strains of Candida and Rhodotorula and are most particularly useful against the opportunistic human pathogen *Candida albicans*. The compositions can in general be employed in any fungal habitat in which the SAFP and the antibiotic retain activity.

The present invention further provides DNA sequences which encode SAFPs. These sequences are useful for expression in transgenic organisms. In particular, the invention provides transgenic plants which express SAFPs from DNA sequences inserted into plant cells, said sequences being under the regulatory control of promoters which function in plants. Preferred promoters are those which are expressed constitutively, in a cell-specific or tissue-specific manner, or in response to pathogen attack or wounding. Any promoter expressible in plant cells is, however, a suitable promoter for use in transgenic plants.

BRIEF DESCRIPTION OF THE FIGURES

FIG. 4 is a photograph of an SDS-polyacrylamide gel electrophoresis run under nonreducing conditions of protein fractions from the CM-Sephadex™ separation (FIG. 2) and phenyl-Sepharose™ separation (FIG. 3). Panel A, lanes 1 to 5, contain approximately 5 g samples of CM-Sephadex™ column fractions 28, 35, 43, 48 and 52, respectively. Panel A, lanes 6–8, contain approximately 5 g samples of combined fractions 42–48 from the CM-Sephadex™ column, and phenyl Sepharose™ peaks 1 and peak 2 (FIG. 3), respectively. Five-fold higher concentrations of these same samples are contained in Panel A, lanes 9–11. Panel B contains two separate phenyl Sepharose™ column isolates of peak 1 (lanes 1 and 2), two isolates of peak 2 (lanes 3 and 4) and a single isolate of peak 3 (lane 5). Panels A and B also contain molecular weight standards as indicated.

DETAILED DESCRIPTION OF THE INVENTION

The term synergy as used herein applies to the enhancement of antifungal activity of certain antibiotics by certain plant proteins, SAFPs. Synergy can be quantitatively measured as the lowering of the minimum inhibitory concentration (MIC) of an antibiotic effected by combining it with an SAFP and is specifically measured herein as enhancement of the activity of antimycotics against *Candida albicans* in in vitro assays. When used herein, the term significant enhancement of antifungal activity refers to enhancements of 10-fold or greater. The MIC is generally defined as the highest dilution (i.e. lowest concentration) of an agent that inhibits growth of a microorganism. In liquid medium, the MIC is usually defined as the lowest concentration of an agent which prevents visible growth of a standard inoculum which is measure by culture turbidity. Inhibition plate assays in which discs impregnated with an antimicrobial agent are placed on microbial lawns can also be used to access MICs (diffusion disc assays). As described in Example 2, the MIC in disc diffusion assays is defined as the lowest concentration of an agent applied to a disc which gives a measurable zone of growth inhibition of the microbial lawn. MICs are determined empirically and often display strain and media dependence.

The effectiveness of an antibiotic agent in vivo is generally assessed in animal model systems, such as those described in Pope and Davies (1979) supra; and Chalkley et al. (1985) supra. In such experiments, effectiveness is assessed as survival or cure rate. Comparisons of the effectiveness of different antibiotic agents is assessed as increases in survival or cure rates.

Figure 1:
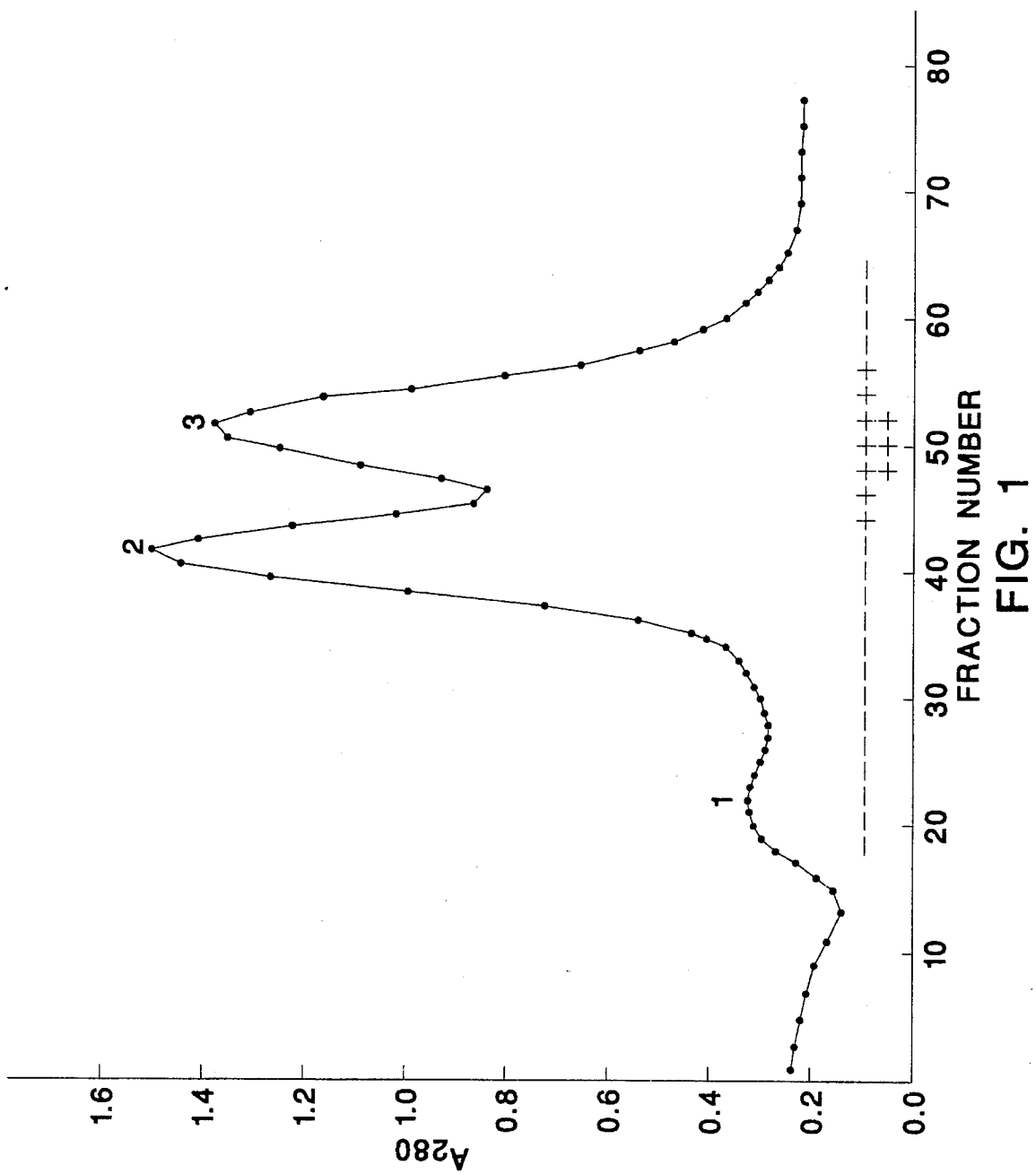
FIG. 1 is an elution profile from the initial CM-Sephadex Pharmacia, Piscataway, N.Y.) column purification step of zeamatin from corn protein extracts. Protein in each 6 ml fraction was quantified by measurement of absorbance at 280 nm. Bound protein was eluted with a linear salt gradient (0.01–0.2M NaCl). One minor and two major protein peaks were eluted. The results of anti-*Candida albicans* synergy assays of nikkomycin Z by individual fractions are given beneath the protein fraction profile. Synergy is quantified as strong inhibition (++), weak inhibition (+) and no inhibition (−) of *C. albicans* in synergy plate assays. Nikkomycin Z synergy was assayed on *C. albicans* suspension plates (carrot juice agar medium) by adding 30 l of a 1:10 dilution of each column fraction with 25 ng of antibiotic to assay discs. Only the third peak contained synergistic activity. Fractions 48–55 contained the majority of the desired activity and were combined for further purification.

The present work is an extension of experiments with antifungal proteins (AFPs) which were isolated from barley, corn and wheat (Roberts and Selitrennikoff (1988) J. Gen. Microbiol. 134:169–176). These proteins inhibited growth of Trichoderma, Phycomyces and Alternaria and have been shown to have endochitinase activity. Wheat and barley AFP chitinases did not inhibit growth of Neurospora, in contrast to corn AFP preparations. Growth of the important human pathogen *Candida albicans* was found to be resistant to inhibition by the AFPs in agar plate assays. AFPs were then assessed to determine if they synergized with antifungal antibiotics to lower the MICs of the antibiotics. Selected results of such experiments are summarized in Table 1. Nikkomycin, a mixture of nikkomycin Z and X, synergized with all AFP preparations, but synergy was particularly dramatic with corn-AFP preparations. Polyoxin synergized significantly with corn and wheat AFP preparations, while modest synergy was observed with combinations of amphotericin and AFP preparations from barley and corn. In contrast, no synergy was observed with papulocandin and AFP preparations. Wheat and barley AFPs (Table 1) were purified to homogeneity. The corn-AFP preparation (Table 1) when chromatographed through a CM-Sephadex™ column was shown to contain multiple protein peaks (FIG. 1). Using synergy with nikkomycin to inhibit the growth of *C. albicans* as an activity assay, the synergizing activity in corn-AFP preparations was found to reside in a single protein fraction from CM-Sephadex™ column chromatography, see FIG. 1. Further purification of this fraction using conventional hydrophobic column chromatography with phenyl-Sepharose™ resulted in the isolation of an approximately 22 kd protein. The 22 kd protein which effected strong enhancement of nikkomycin activity was designated a corn-SAFP, and specifically named zeamatin.

TABLE 1

Effect of AFP preparations on Antibiotic MIC against *Candida albicans*
MIC against *Candida albicans* (g/disc)

| AFP[a] | Nikkomycin | Papulacandin | Polyoxin B | Amphotericin B |
|---|---|---|---|---|
| None | 0.17 | 0.5 | 50.0 | 5.0 |
| Barley | 0.05 (3×)[b] | 0.5 | 50.0 | 1.6 (3×) |
| Blue corn | <0.0017 (>100×) | 0.5 | 5.0 (10×) | 1.6 (3×) |
| Yellow corn | <0.0017 (>100×) | 0.5 | 5.0 (10×) | 1.6 (3×) |
| Wheat | 0.05 (3×) | 0.5 | 5.0 (10×) | 5.0 |

Figure 2A:
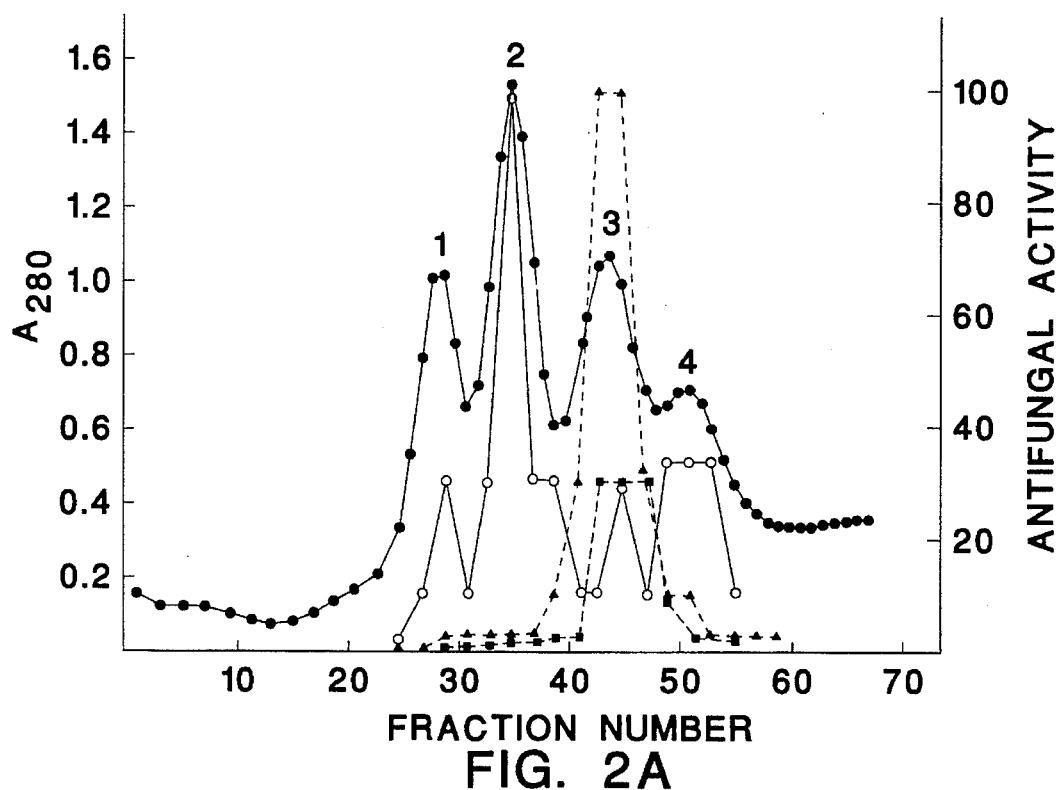
FIG. 2A displays the quantitative results of antifungal assays, while FIG. 2B displays the quantitative results of enzyme assays across the four peaks. Absorbance at 280 nm is represented in both A and B by closed circles, solid lines. The results of hyphal extension inhibition of *T. reesei* (open circles, solid line), hyphal extension inhibition of *N. crassa* (closed squares, dashed lines) and synergistic anti-Candida activity (closed triangles, dotted line) are presented on panel A. The results of chitinase (closed triangles, dotted line), glucanase (open squares, solid line) and β-N-acetyl-hexosaminidase (closed circles, dashed line) assays are presented in panel B.
Figure 2B:
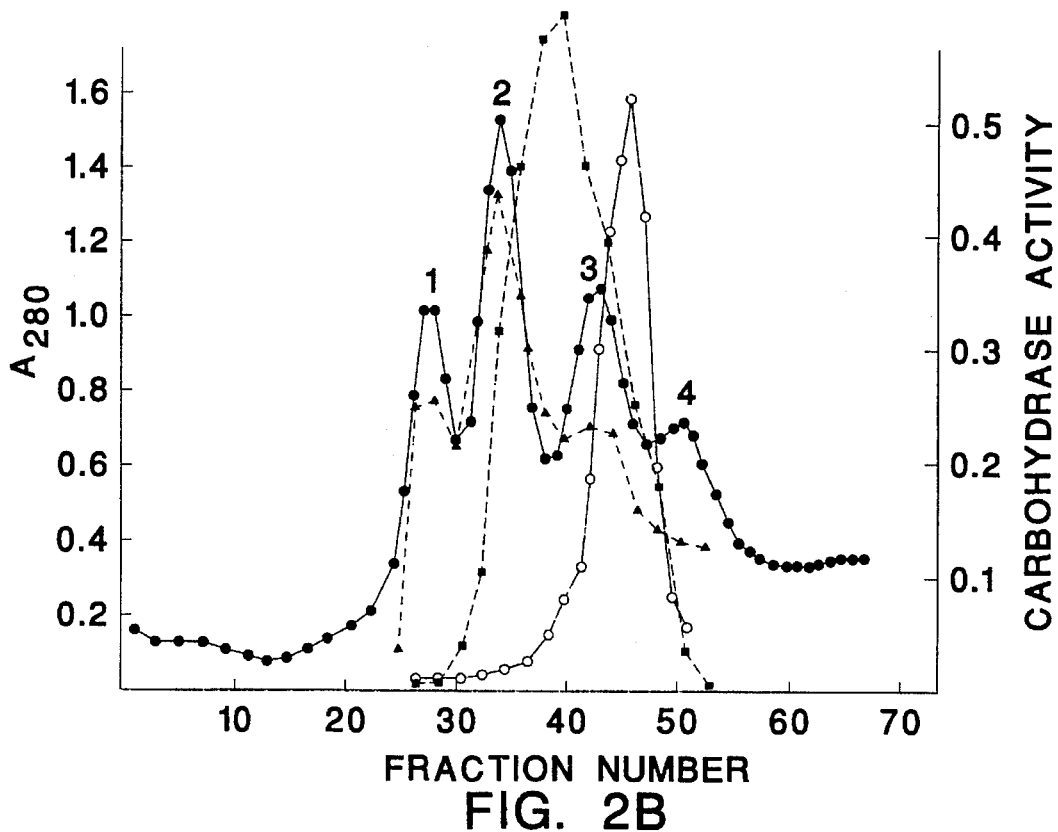
FIG. 2 shows elution profiles from CM-Sephadex™ column purification of zeamatin from corn protein extracts. A flow rate of 1 ml/min was employed in these separations. Protein in each 6 ml fraction was quantified by measurement of absorbance at 280 nm. Bound protein was eluted with a linear salt gradient (0.01 0.2M NaCl). Four peaks were eluted.

[a]AFP preparation was supplied at 15 g protein/disc. AFP fractions were prepared as described in Roberts and Selitrennikoff (1987) J. Gen. Microbiol., supra.
[b]The number in parentheses refers to the fold reduction in MIC Since a significant loss in specific synergizing activity was observed in the conventional phenyl-Sepharose™ chromatography step, efforts were made to improve the purification of corn-SAFP activity. Improved purification of zeamatin was obtained by carrying out the CM-Sephadex™ chromatography at a slower flow rate than had been employed in previous separations and more importantly, by employing a novel phenyl-Sepharose™ chromatographic procedure. Slower elution in the CM-Sephadex™ step resulted in four distinct protein peaks (FIG. 2) rather than the three peaks observed previously (FIG. 1). Synergistic anti-Candida activity was found only in peak 3. Anti-Neurospora activity was also confined to peak 3, while anti-Trichoderma activity was observed in all peak fractions. All four peaks were also assayed for chitinase, glucanase and β-N-acetylhexosaminidase activity. None of these enzyme activities coincided with the anti-Neurospora or synergistic anti-Candida activity of peak 3.

Zeamatin was then further purified employing a novel method of hydrophobic column chromatography. Fractions from the CM-Sephadex™ column that contained synergistic anti-Candida activity were combined and subjected to phenyl-Sepharose™ column chromatography. This separation was carried out by loading the column at a lower salt concentration than is typically employed in order to reduce the hydrophobic interactions between the proteins and the column. Bound protein was then eluted with 50% ethylene glycol. This procedure resulted in the profile of FIG. 3 containing three bands, one of which passed directly through the column (1), a second which was somewhat retarded (2), and a third smaller band which was eluted with 50% ethylene glycol (3). SDS-PAGE electrophoresis (FIG. 4) demonstrated that peak 2 from the low salt phenyl-Sepharose™ separation contained an apparently homogeneous 19 kd protein (zeamatin), as determined by gel-electrophoresis under nonreducing conditions. When run in gel-electrophoresis under reducing conditions, this 19 kd protein ran as an apparently homogeneous 22 kd protein. This peak 2 was also demonstrated (see Table 2) to contain all synergistic antifungal activity as well as all anti-Neurospora activity. Peak 2 also contained anti-Trichoderma activity.

TABLE 2

Antifungal and Enzymatic Activities of Proteins Purified by Phenyl-Sepharose ™ Chromatography

| Fraction Assayed | Chitinase Activity[a] | Glucanase Activity[b] | Anti-Trichoderma Activity[c] | Anti-Neurospora Activity[c] | Anti-Candida Activity[c] |
|---|---|---|---|---|---|
| Combined fractions (FIG. 3) | 3.5 | 84 | 0.5 | 1 | 0.9 |
| Peak 1[d] | 2.9 | 9 | 0.5 | >5 | >10 |
| Peak 2[d] | NA[e] | 1 | 3 | 0.3 | 0.2 |
| Peak 3[d] | NA[e] | 2010 | NA[e] | NA[e] | — |

[a] Reducing sugar released after incubation at 37° for 4 h (moles glucose/mg protein).
[b] Reducing sugar released after incubation at 37° for 20 min. (moles glucose/mg protein).
[c] Minimum amount of protein required to inhibit fungal growth (g protein/disc) in the presence of sub-inhibitory levels of nikkomycin.
[d] Protein peaks from chromatography in 0.1 M NaCl (FIG. 2)
[e] NA = activity detected.

The association of synergistic anti-Candida activity with zeamatin was confirmed by a bioautography experiment in which substantially pure protein of peak 2 (FIG. 3) was subjected to electrophoresis of pH 6.0 in a nonreducing acrylamide gel. The protein from this gel was allowed to diffuse into an agar plate containing freshly seeded *C. albicans* and sub-inhibitory concentrations of nikkomycin. A strong zone of growth inhibition was observed only at a position in the agar which coincided with the zeamatin protein band. This bioautography procedure has also been employed to demonstrate the association of synergistic anti-Candida activity with the sormatin and avematin protein bands.

Early experiments demonstrated that zeamatin could be extracted from cornmeal using 0.05M acetic acid, and that it was stable at moderate temperatures. Thus, it seemed possible that corn-SAFP might survive the low pH and elevated temperatures of the corn steeping process and be present in an active form in steepwater. Accordingly, steepwater samples were obtained from the Adolph Coors corn refining plant, Johnstown, Colorado, and analyzed for antifungal activity. The 35-hour light steepwater sample was effective at inhibiting growth of *Trichoderma reesei* and *Candida albicans* in the presence of sub-inhibitory levels of nikkomycin. This activity was lost following heating at 90° C. for 15 minutes. Analysis of the proteins in steepwater by SDS-PAGE under nonreducing conditions showed a broad protein smear accompanied by a distinct protein band at 19 kd. This protein band corresponds with the 22 kd zeamatin band observed under reducing conditions. The synergistic anti-Candida activity of the extract indicated that zeamatin was intact and active in steepwater. These experiments are of interest because they identify corn steepwater as a potential commercial source for the large scale isolation of zeamatin.

Additional experiments showed that the synergistic antifungal and antifungal activity in steepwater could be precipitated using ammonium sulfate, ethanol, or acetone. Moreover, testing these concentrated preparations on a number of fungal plant pathogens showed that they inhibited growth on agar of pathogenic strains of Trichoderma, Rhizoctonia, and Fusarium.

SAFPs have been identified in sources other than corn. Seeds are known to synthesize large mounts of new enzymes (e.g., glucanases) on germination. Accordingly, wheat and rye were allowed to germinate for three days, after which protein extracts were prepared as in AFP preparations. These protein extracts were found to contain high SAFP activity and were found to lower the MIC of nikkomycin against *C. albicans* by about 100-fold. The wheat and rye SAFPs could be partially purified by the same procedure used for corn-SAFP. However, the wheat and rye SAFP preparations, in contrast to preparations from corn, lost activity after several days storage at 4° C. and have not as yet been further characterized.

Similar to zeamatin preparations, sorghum and oat extracts were found to contain SAFP activity that was stable. Sormatin was purified to apparent homogeneity using methods similar to those employed to purify zeamatin. Avematin has been partially purified to homogeneity or near homogeneity from partially purified materials described herein by application by application of methods applied to the purification of zeamatin or sormatin, or by application of methods known to the art of protein purification.

Chitinase and glucanase preparations from several other sources were also tested in the synergy assay. No synergy with nikkomycin was found with chitinases from *Serratia marcescens*, *Pseudomonas stuzeri*, or *Streptomyces griseus* or in glucanase preparations from Penicillium or mollusk. Significant synergy was observed, however, with a partially purified glucanase preparation from the fungus Rhizopus and in commercial bacterial (*Arthrobacter luteus*) enzyme mixture containing both chitinase and glucanase called Zymolase (available from Sigma Chemical Co., St. Louis, Mo.). The nature of the synergizing enzymes in these preparations has not been identified, and it is not known whether they act by a mechanism that is similar to plant SAFPs. The synergizing activity in these preparations may be due to minor components in the mixtures.

The anti-Candida synergy that is observed with the SAFP/antibiotic compositions of the present invention is surprising, since it is not predictable that a particular combination of two antimicrobial agents, even those which have different modes of action, will be synergistic.

The very strong synergy observed in the zeamatin/nikkomycin compositions of the present invention against Candida strains was also surprising. Typically, enhancements due to synergy are observed to be in the range of 10 fold or less. For the zeamatin/nikkomycin compositions, the MIC of nikkomycin was lower by up to 100 fold in plate assays. In similar inhibition assays of *Candida albicans* done in liquid media, the MIC of nikkomycin was also lowered by up to about 100 fold (Table 3).

TABLE 3

| Nikkomycin in Wells (g/ml) | Growth Inhibition of *C. albican* in Liquid Culture — Zeamatin in Wells (g/ml)[A] | | | | | | | |
|---|---|---|---|---|---|---|---|---|
| | 0 | 0.3 | 1.0 | 3.0 | 10 | 30 | 100 | 300 |
| 0 | | | +++ | +++ | +++ | +++ | + | − |
| 0.017 | | +++ | +++ | +++ | +++ | − | − | − |
| 0.050 | | +++ | ++ | ++ | ++ | − | − | − |
| 0.17 | | +++ | − | − | − | − | − | − |
| 0.5 | | +++ | − | − | − | − | − | − |
| 1.7 | | +++ | − | − | − | − | − | − |
| 5 | | + | − | − | − | − | − | − |
| 17 | | − | − | − | − | − | − | − |

[A]Each well contained 150 l of 2% carrot juice inoculated with *C. albicans* suspension to give an absorbance at 630 nm of 0.005. Fungal growth was scored as +++, ++, + or no growth (−) after visual inspection for turbidity.

Zeamatin/nikkomycin compositions were found to be effective against several strains of *C. albicans* which varied in their sensitivity toward nikkomycin (Table 4). In each case, zeamatin significantly synergized the effect of nikkomycin and lowered the MIC of nikkomycin in compositions by about 33 to 100 fold. Zeamatin/nikkomycin compositions were found to be effective against *Candida albicans* on either poor or rich medium. Zeamatin synergized nikkomycin activity of nikkomycin has been found to be attenuated by peptide inhibition.

The mechanism by which SAFP synergizes the action of polyoxins, nikkomycins and amphotericins is not known. It was thought that SAFP might act to increase penetration of the antibiotics into the target fungi. This could occur as the result of degradation or permeabilization of the fungal cell wall by SAFP. Fungal cell walls are composed of chitin, glucans with β-1,3 or β-1,6- linkages and mannans with α-1,6, α-1,2 or α-1,3-linkages. It has been demonstrated, however, that zeamatin, unlike other antimycotic agents, does not have chitinase, glucanase or mannanase activity. A more probable mechanism, supported by experiments described below, is that SAFP permeabilizes the fungal cell membrane. It is suggested that SAFP lyses fungi by direct insertion of the protein into fungal membranes to form transmembrane pores. Amphiphilic polypeptides may bind to cells through a cationic region of the molecule followed by insertion of a hydrophobic domain through the lipid bilayer of the membrane. For example, zeamatin's amphiphilic nature is suggested by the protein's late elution from CM-Sephadex™ (a cationic property) and its retarded passage through phenyl-Sepharose™ (a hydrophobic property). That zeamatin acts via cell membrane permeabilization is further supported by the rapid effect of low concentrations of SAFP's on fungi, even at 0° C. For example, 1 g/ml zeamatin induces hyphal rupture in less than 15 seconds at 23° C. This rapid rupture suggests a non-enzymatic mechanism of action. The operability and utility of the SAFPs of the present invention are, however, not dependent upon these suggested mechanisms, and the practice of the present invention does not require characterization of the specific activity of an SAFP. Similarities in structure (similar molecular weights, similar elution behavior on chromatography and homologies in N-terminal sequence) of zeamatin, sormatin and avematin, and more importantly, their common function in synergism of anti-fungal activity, indicate that these proteins and other protein strains displaying this function represent a class of proteins (SAFPs) which act by an analogous mechanism.

In the course of conducting experiments to determine zeamatin's mechanism of action on fungi, the ability of zeamatin to inactivate ribosomes was assessed. Ribosome inactivating proteins (RIPs) had been isolated from grains including corn (Coleman and Roberts (1981) supra). Zeamatin was tested as described in Coleman and Roberts (1981) supra, for its ability to inhibit protein synthesis in Neurospora cell-free extracts. Addition of up to 10 g/ml of zeamatin to this in vitro protein synthesis assay had no inhibitory effect. In contrast, RIP isolated from corn (Coleman and Roberts (1981) supra) inhibits ribosomes at a level of 0.06 g/ml. Furthermore, corn-RIP purified as described in Coleman and Roberts (1981) supra was found to have no synergistic antifungal activity in Candida plate assays employing nikkomycin. Specifically, addition of up to 1500 g/ml of corn-RIP displayed no synergy with nikkomycin. It should be noted that greater than 90% of corn-RIP activity was found to reside in the 55%–85% ammonium sulfate fraction prepared from cornmeal extract, while 90% of the zeamatin activity was found to reside in the 30 %–55% ammonium sulfate fraction.

Since purified zeamatin contained no detectable enzymatic activity associated with fungal cell wall degradation, the action of zeamatin on the fungal cell membrane was examined. Several experimental approaches were used to examine whether the fungal membrane was the site of action of zeamatin (and by analogy the site of action of other SAFPs from grain). The release of ultraviolet-absorbing material from suspension of *C. albicans* was examined (see FIG. 8a). It was found that as little zeamatin as 1 g/ml produced detectable cell leakage. A second leakage experiment (FIG. 8b) was performed by preloading *N. crassa* cells with [$^{14}$C]-aminoisobutyric acid, a non-metabolizable amino acid used to measure membrane integrity (Georgopapadakou et al. (1987) Antimicrob. Agents Chemother. 31:46–51) and following its release from cells upon treatment with zeamatin or amphotericin B, which antibiotic is known to permeabilize fungal membranes. Incubation of *N. crassa* with zeamatin at 30° C. caused an immediate release of radioactivity which was complete by 3 min. At 0° C., release was slower, but 80% of the radioactivity was lost from cells by 20 min. By comparison, amphotericin B produced fairly rapid leakage at 30° C., but no cell leakage at 0° C. (It had been noted by Gale (1974) J. Gem Microbiol. 80:451–465 that amphotericin did not permeabilize cells at 0° C. and this effect was attributed to immobility of the membrane lipid and or a requirement for metabolic energy.) The basic proteins lysozyme and pancreatic ribonuclease were found to have no effect on membrane permeability of *N. crassa*. Zeamatin was found by microscopic examination to induce hyphal rupture in germinated spores of *N. crassa*.

Incubation with zeamatin produced hyphal that stained with methylene blue and were vacuolated. Hyphal rupture occurred in less than 15 s at 23° C. with as little as 1 g/ml zeamatin. Most, but not all, ruptures were observed at hyphal tips or immediately behind the hyphal apical dome, which are regions that are susceptible to turgor pressure. These results indicate that SAFP acts to permeabilize the fungal plasma membrane.

Figure 8A:
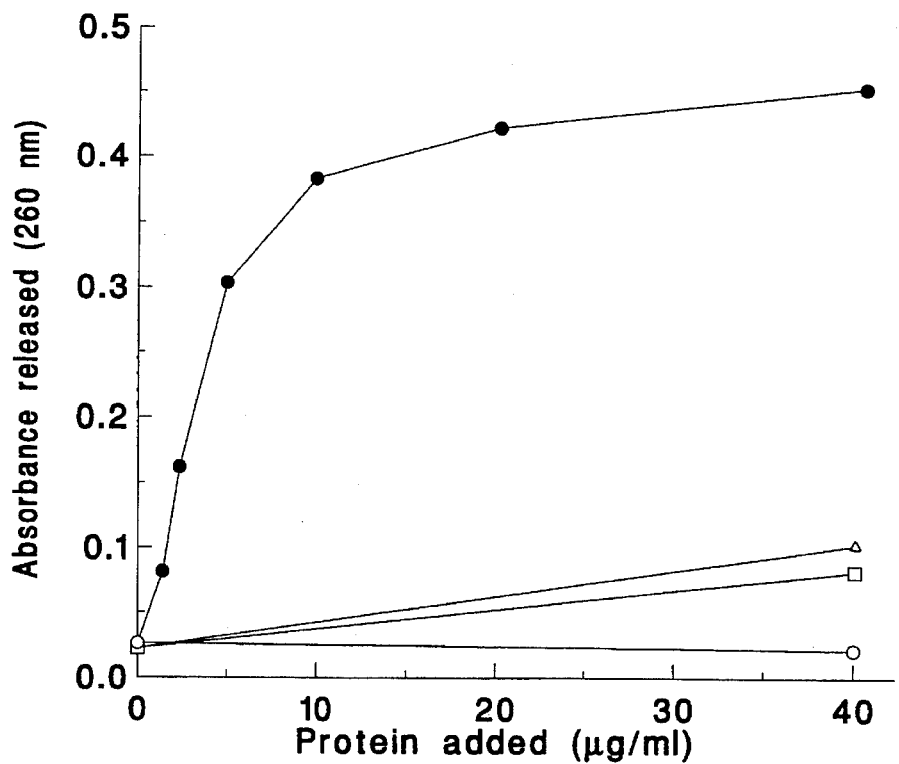
FIG. 8 includes graphs showing the results of experiments testing the effect of zeamatin on membrane permeabilization. View (a) is a graph showing the release of ultraviolet-absorbing material measured as absorbance at 260 nm from *C. albicans* as a function of added protein (g/ml). *C. albicans* was incubated at 37° C. for 30 min with the indicated concentrations of zeamatin (closed circles), lysozyme (closed triangles), cytochrome C (open squares) or bovine serum albumin (open circles). View (b) is a graph of the release of radiolabelled aminoisobutyric acid with time from *N. crassa* on incubation with the given agent (12 g/ml) at the indicated temperature (30° C. or 4° C.): zeamatin at 30° C. (closed circles), zeamatin at 4° C. (open circles), amphotericin B at 30° C. (closed squares), amphotericin B at 4° C. (open squares), pancreatic ribonuclease at 30° C. (closed triangles) and lysozyme at 30° C. (crosses).
Figure 8B:
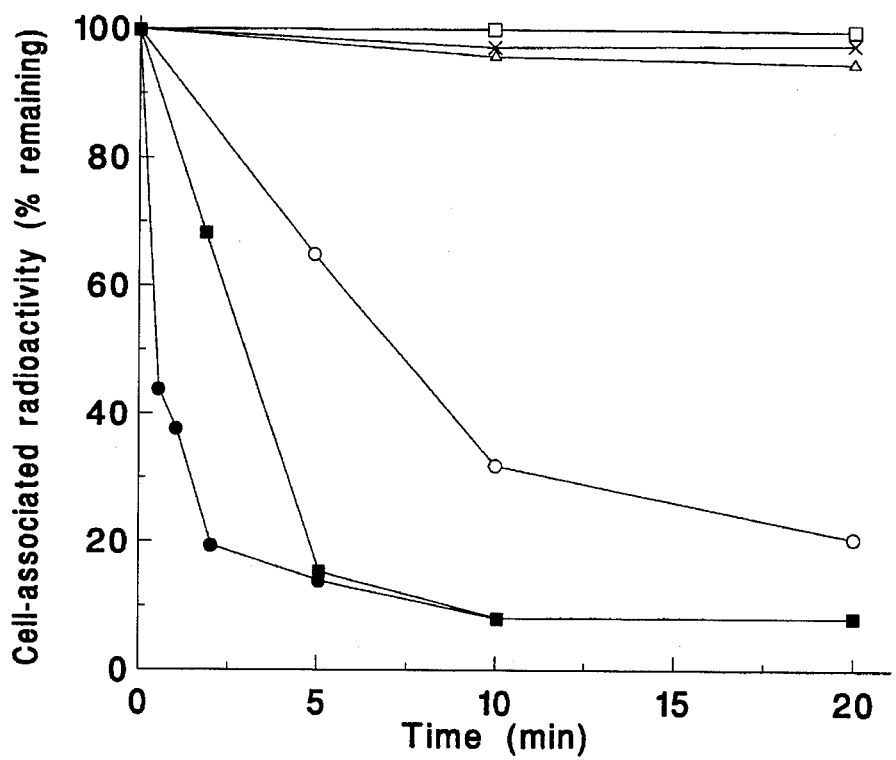

Certain basic proteins had previously been shown to cause release of cytoplasmic components from Candida (Yphantis et al. (1967). However, in contrast to the effect of SAFP, the protein concentrations required to cause such release are relatively high as can be seen from the limited release caused by additions of 40 g/ml lysozyme, cytochrome C or bovine serum albumin (FIG. 8a).

The results of the release experiments of FIG. 8 and the effect of SAFP on hyphae are consistent with a fungal lysing mechanism mediated by direct insertion of the SAFP protein into fungal membranes to form transmembrane pores. A variety of proteins have been shown to lyse mammalian cells by such a mechanism ((Yphantis et al. (1967) J. Bacteriol. 94:1509–1515; Bhakdi and Tranum-Jensen (1987) Reviews of Physiology, Biochemistry and Pharmacology 107:147–223). In addition, polypeptides and proteins have been isolated from a number of sources which appear to lyse microorganisms by a similar mechanism, including melittin (bee venom, Mackler and Kreil (1977) Inflammation 2:55–65), cecropins (insect haemolymph, Steiner et al. (1985) Nature 292:246–248), magainins (toad skin, Zasloff (1987) Proc. Natl. Acad. Sci. 845449–5453) and thionins (Bohlmann et al. (1988) EMBO J. 7:1559–1565). Thionins differ from SAFPs of the present invention in that they are described as relatively low molecular weight polypeptides (~5,000 Mv) occurring in seeds and leaf tissue in cereals, such as barley. Further, they are described as having a general toxic effect on bacterial, fungi and small animals. Synergistic antifungal activity has not been attributed to thionins. Finally, thionins have no apparent sequence homology to SAFPs. In addition, larger proteins like the bacteriocins: colicin (Parker et al. (1989) Nature 337:93–96) and halocin (Torreblanca et al. (1989) J. Gen. Microbiol. 135:2655–2661) and the complement attack complex described by Bhakdi and Tranum-Jensen (1987) supra are reported to act by this mechanism. Many of these polypeptides and proteins have amphiphilic properties, and may act by binding to cells through a cationic region of the molecule followed by insertion of a hydrophobic domain through the lipid bilayer of the membrane.

Substantially pure zeamatin and sormatin were subjected to conventional protein sequencing techniques. An initial determination of the partial amino acid sequences of these proteins is given in Table 5. A computer search for protein sequences having homology to the SAFPs was performed. Homology was found to thaumatin, an intensely sweet protein from *Thaumatococcus danielli* (see, Edens et al. (1982) Gene 18:1–12), pathogenesis-related (PR) proteins, for example from tobacco (see, Cornelissen et al. (1986) Nature 321:531–532) and osmotin, a tobacco protein associated with the plant's adaptation to salt (Singh et al. (1987) Plant Physiol. 85:529–536). Particularly striking homology was found between the N-terminal region of zeamatin and sormatin and that of a maize proteinase/amylase inhibitor, designated MAI, reported by Richardson et al. (1987) Nature 327:432–434. A comparison of the N-terminal sequences of MAI, thaumatin, tobacco PR and osmotin is included in Table 5. The sequence reported in the Richardson et al. (1987) reference (supra) is attributed to a maize protein which displays in vitro inhibition of bovine trypsin and insect α-amylases are reportedly not inhibited by MAI.) This maize bifunctional inhibitor, MAI, is reported to contain 206 amino acids which corresponds to a Mr of 22,077 and is noted to contain a high content of cystein. The N-terminal amino acids of zeamatin. Sormatin differs from zeamatin and MAI at 2 amino acids in the first 22 N-terminal amino acids. The sequence homologies observed between the SAFPs and MAI is surprising, given their distinct biological activities. Substantially pure zeamatin and sormatin have been assayed for inhibition of trypsin as described in Richardson et al. (1987) supra, and found to have no such activity. No antifungal or antimicrobial activity has been attributed to MAI. Richardson et al. (supra) pointed out that MAI had significant homology to thaumatin and PRs induced in tobacco plants in response to viral infection. The functions or activities of thaumatin and PRs have not yet been determined. Richardson et al. suggested that thaumatin and PRs and other proteins homologous to MAI should be assessed for inhibition of hydrolytic enzymes. Richardson et al. note that other workers (Pierpont et al. (1987) Physiol. Mol. Pl. Pathol. 31:(2)291–298 were not able to detect trypsin inhibition by PR.

From the amino acid sequence of zeamatin determined as described above, oligonucleotides were designed for the purposes of cloning the zeamatin cDNA using the polymerase chain reaction (PCR) and the screening of a cDNA library. The cloned and sequenced zeamatin cDNA is shown in Table 7 (SEQ ID NO: 7). Using similar techniques of protein sequence determination, PCR and library screening cDNAs for other SAFPs including sormatin and avematin are similarly obtainable. These cDNAs are expressible in transgenic organisms under the control of promoters which are known to be active in the target cells. Thus, for expression in transgenic plants the cDNAs can be inserted into plant cells under the control of a promoter known to be expressible in plant cells. Typically such an "expression cassette" would have the following components: (1) a promoter expressible in plant cells, (2) DNA sequence encoding the SAFP protein, or sequence with substantial homology thereto, and (3) a transcriptional terminator. SAFPs such as zeamatin may already include in their cDNA an aminoterminal sequence which serves to target the mature SAFP to the apoplast. However, where such a component of the cDNA may be absent this may be added to the expression cassette by including: (4) a corresponding extracellular targeting sequence encoding a signal peptide from a different gene (e.g. PR1) fused to the amino terminus of the SAFP. Alternatively, for cytosolic localization this sequence may be omitted or disrupted if a native signal peptide exists. A further component which can be included in the expression cassette is (5) a sequence fused to the carboxyterminus, typically required together with the amino terminal sequence of (4) which may serve to target the SAFP to the cell vacuole. Techniques for the transfer of expression cassettes to plant cells are well known in the art. Preferred procedures for dicotyledonous plant species involve the use of *Agrobacterium tumefaciens* and corresponding binary vectors (Alexander et al., (1993) PNAS 90:7327–7331). Preferred procedures for monocotyledonous plant species involve direct gene transfer with corresponding vectors. See, for example, Koziel et al., Biotechnology 11:194–200 (1993).

Zeamatin and sormatin are not sweet-tasting and no antifungal activity could be demonstrated with thaumatin against *N. crassa*, *C. albicans* or *T. reesei*. No synergistic antifungal activity against *C. albicans* could be demonstrated with thaumatin.

It is important to note when considering the relationship between protein structure and function that small structural changes in structure are known to affect antifungal activity. For example, the human neutrophil defensin HNP-1 effectively kills *C. albicans*, whereas HNP-3, which differs from HNP-1 only in its amino terminal amino acid, does not (Selsted et al. (1985) J. Clin. Invest. 76:1436–1439).

TABLE 4

Comparison of Growth Inhibition of Various
strains of *Candida albicans* on
Different Growth Media
MIC Nikkomycin Z[1]

| Candida strain | Carrot Juice Agar | | Nutrient Agar | |
|---|---|---|---|---|
| | Nikk | Nikk Zeamatin[2] | Nikk | Nikk/ Zeamatin[2] |
| I[3] | 170 | 1.7 | 1500 | 15 |
| II | 170 | 1.7 | 5000 | 50 |
| III | 50 | 0.5 | 500 | 15 |
| IV | 17 | 0.5 | 170 | 5 |

[1]Minimum Inhibitory Concentration (MIC) of nikkomycin Z in units of ng/disc. All plates were incubated for 16 h at 37° C.
[2]In assays of Nikk/zeamatin, the concentration of zeamatin was 15 g/disk. Zeamatin was partially purified through the CM-Sephadex™ step (fraction CMS).
[3]I is laboratory strain B-311 and strains II–IV are separate clinical isolates.

TABLE 5

N-Terminal Amino Acid Sequences of Grain SAFPs and Several Homologous Proteins[A,B]

| | |
|---|---|
| Sormatin | A V F T V V N R C P Y T V W A A S V P V ----- G G |
| Zeamatin | A V F T V V N Q C P F T V W A A S V P V ----- G G G R Q L N R G E (SEQ ID NO: 1) |
| MAI | A V F T V V N Q C P F T V W A A S V P V ----- G G G R Q L N R G E |
| TPR | A T F D I V N Q C T Y T V W A A A S P ------ G G G R Q L N S G Q |
| THA | A T F E I V N R C S Y T V W A A A S K G D A A L D A G G R Q L N S G E |
| Osmotin | A T I E V R N N C P Y T V W A A S T P I ----- G G G R R L D R G Q |

[A]MAI is the bifunctional inhibitor described in Richardson et al. (1987) supra; TPR is a tobacco pathogenesis-related protein; and THA is thaumatin, whose sequence is taken from that given in Richardson et al. (1987) supra; osmotin sequence is taken from Singh et al. (1987) supra.
[B]Sequences are aligned for maximum overlap.

The following examples are intended for illustrative purposes only and are not intended to limit the scope of the invention.

EXAMPLE 1

Isolation and Purification of Zeamatin from Corn

Antifungal protein (AFP) extracts, containing SAFP and other antifungal proteins, were prepared from corn using methods similar to those described in Roberts and Selitrennidoff, 1986 (supra). The initial protein extraction was carried out at 4° C. essentially without loss of activity. Corn meal was obtained either from the refrigerator section of health food stores or by grinding dried corn finely in a coffee grinder. AFP could be extracted from corn meal using either acidic or neutral pH buffers (pH ranging from about 4.0 to 7.0) In a typical extraction, corn meal (2 lbs) was stirred for 1 h at 4° C. in 2 l of 50 mM NaCl/25 mM sodium phosphate (pH 7.0)/5.0 mM EDTA. The resulting suspension was centrifuged (10,000×g, 20 min, 4° C.) and the supernatant protein extract was saved.

Ammonium sulfate was slowly added with stirring to the corn protein extract, to obtain a 30% saturated solution which was left overnight at 4° C. The solution was then centrifuged (10,000× g, 20 min) and the supernatant was made 55% saturated with ammonium sulfate. The solution was left 20 min at 4° C. and centrifuged (10,000×g, 20 min). The precipitate pellet from the 55% saturated ammonium sulfate solution was saved and then resuspended in 80 ml of 10 mM NaCl/5.0 mM sodium phosphate (pH 7.0)/1.0 mM EDTA resuspension buffer. The resuspended 30%–55% protein fraction was then clarified by centrifugation and dialyzed (16 h, 4° C.) against 2×1l of resuspension buffer.

The dialyzed solution was again clarified by centrifugation prior to further purification by chromatography on carboxymethyl-Sephadex™ (CM-Sephadex™). CM-Sephadex™ column chromatography was carried out at 23° C. The dialyzed protein fraction, was passed through a CM-Sephadex™ column (C-50-120, from Sigma Chemical Co., St. Louis, Mo.) equilibrated with resuspension buffer. The column was prepared by soaking 2 g of column material in resuspension buffer and adding the slurry to a column to form approximately 60 ml of packed gel volume. The dialyzed protein fraction was washed through the column with buffer until the absorbance of the effluent at 280 nm had fallen to approximately 0.2; typically this required washing with about 400 ml of buffer. In a typical preparation, about 1700 mg of protein was added to the column, of which ⅔ washed through and ⅓ remained bound. All of the AFP activity remained bound to the column.

Antifungal protein was then eluted from the column using a linear salt gradient prepared conventionally by running 220 ml of 200 mM NaCl/5 mM sodium phosphate (pH 7.0)/1 mM EDTA into 220 ml of resuspension buffer. Fractions (6 ml) were collected at 3-minute intervals. This gradient eluted three protein peaks (as assayed by absorbance at 280 nm) as shown in FIG. 1; one minor component eluting early and two major components eluting later. The latest eluting peak contained all of the SAFP activity. Fractions containing the highest synergistic antifungal activity, fractions 48–55 (FIG. 1), were collected, and concentrated 3-fold by ultra-filtration (Amicon YM-10 filter). This fraction, designated fraction CMS, retained antifungal and synergistic antifungal properties and was employed in the in vitro anti-Candida plate assays presented in Table 4 (infra).

Fraction CMS retained antifungal activity against *T. reesei* but did not inhibit *C. albicans* in agar plate assays. This fraction was found to contain all synergistic antifungal activity against *C. albicans*. This fraction as assayed by SDS-PAGE was found to contain several protein peaks, including a peak at about 19 kd (by SDS-PAGE under nonreducing conditions).

Further purification of fraction CMS was initially attempted employing phenyl-Sepharose™ column chromatography employing 1M (NH$_4$)$_2$SO$_4$ at 4° C. Two protein peaks (assayed by absorbance at 280 nm) eluted from the column, the fast after about 8 ml of buffer, the second after about 25 ml of buffer. Synergizing activity was found only in the second protein peak. However, a significant loss (80%) in specific synergizing activity was observed employing this procedure. Electrophoresis of the fraction displaying SAFP activity run using high protein loading (30–50 g protein/land) was found to contain several higher molecular weight bands.

A second procedure was found to result in improved purification of zeamatin. Ammonium sulfate fractionation of corn protein extract was performed as described above. The dialyzed 30%–55% fraction was subjected to CM-Sephadex™ chromatography, essentially as described above. However, the chromatography was carried out at a slower flow rate (1 ml/min), which resulted in the elution of four distinct peaks (FIG. 2). Synergistic anti-Candida activity was confined to peak 3. This peak was also found to contain growth inhibitory activity against *Neurospora crassa*. Anti-Neurospora activity was found only in corn AFP preparations, not in AFP preparations of wheat and barley. Anti-Trichoderma activity was found in all four peaks. Chitinase, glucanase ($\beta$1,3- and $\beta$1,6-) and $\beta$-N-acetylhexosaminidase activities were also assayed across the four peaks. Chitinase was found in all four peaks. A single peak of glucanase activity at fraction 47 and a single peak of $\beta$-N-acetyl hexosaminidase at fraction 40 were detected. Anti-Neurospora and synergistic anti-Candida activity peaked at fraction 44. These antifungal activities did not coincide with any of the enzyme activities tested.

Figure 3:
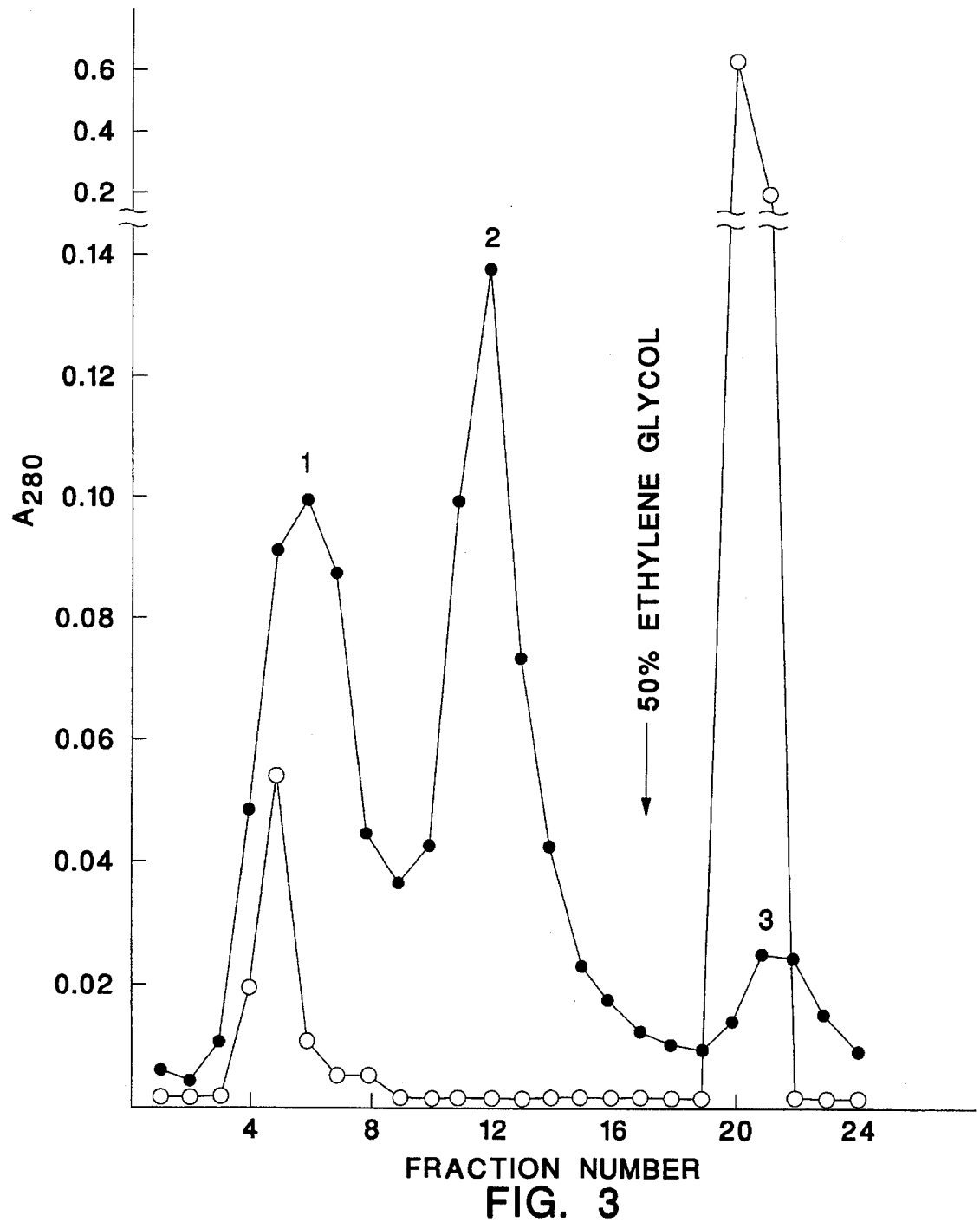
FIG. 3 is an elution profile of phenyl-Sepharose (Trademark, Pharmacia, Piscataway, N.Y.) column chromatograph purification of zeamatin. Equivalent samples of protein from peak 3 (FIG. 2) were washed through the column in 1M ammonium sulfate (open circles) and 0.1M sodium chloride (closed circles) and bound protein was subsequently eluted with 50% ethyl glycol. Protein was quantified by measurement of absorbance at 280 nm.

The fractions associated with synergistic anti-Candida activity (42–48) were combined, concentrated and subjected to further purification. Hydrophobic column chromatography employing phenyl-Sepharose™ (CL-4B from Sigma Chemical Co., St. Louis, Mo.) was used. The sample was loaded onto the column at a low salt concentration employing 0.1M NaCl to reduce the hydrophobic interaction between proteins and the column materials. The elution profile is shown in FIG. 3 (closed circles), compared to the elution profile when higher salt concentrations (1M $(NH_4)_2SO_4$) were employed. A large protein fraction passed directly through the column (peak 1), followed by another large fraction whose passage was retarded (peak 2). A third smaller fraction (peak 3) was then eluted with 50% ethylene glycol.

The three peak fractions from phenyl-Sepharose™ chromatography were assayed for enzyme activities and antifungal activities as shown in Table 2. Peak 1 contained most of the chitinase activity, a small amount of glucanase activity, and most of the anti-Trichoderma activity. No anti-Neurospora or synergistic anti-Candida activity was found in peak 1. Peak 3 contained most of the glucanase activity and no other detectable enzymatic or antifungal activity. Peak 2 contained all of the anti-Neurospora and synergistic anti-Candida activity and a smaller activity against Trichoderma. Peak 2 contained no detectable chitinase activity and a very small amount of glucanase.

Figures 4A, 4B:
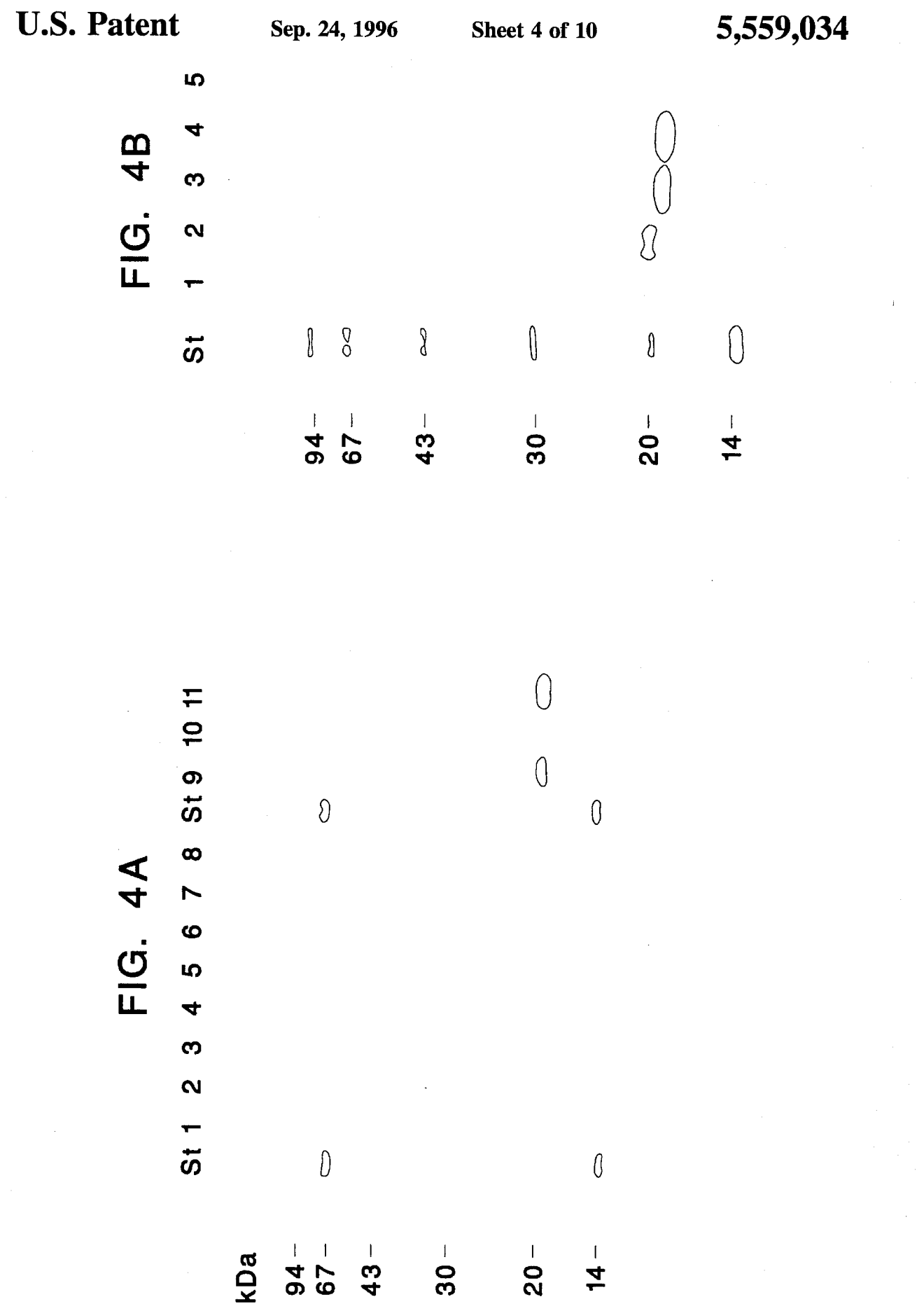

The purity of the various fractions from the CM-Sephadex™ and nonreducing conditions (FIG. 4). Electrophoresis of the CM-Sephadex™ fractions 28, 35, 43, 48 and 52 (FIG. 4A, lanes 1–5 respectively) showed different protein species in the fractions as expected. Combined fractions 42–48, as well as the phenyl-Sepharose™ fractions peak 1 and peak 2, were analyzed at low loading (about 5 g protein/lane, FIG. 2A, lanes 608) and at 5-fold higher loading (lanes 9–11). In addition, two separate phenyl-Sepharose™ chromatography isolates of peak 1 (FIG. 2B, lanes 1 and 2) and peak 2 (FIG. 2B, lanes 3 and 4) and a peak 3 fraction (lane 5) were analyzed. It is apparent that peak 1 contains multiple protein species present in fractions 42–48, peak 2 contains an apparently homogenous 19 kd protein, zeamatin, and peak 3 contains two 30 kd protein species and a small amount of zeamatin. It is estimated at zeamatin isolated in peak 2 of the phenyl-Sepharose™ elution is about 95–98% pure.

The protein material isolated from peak 2 of the phenyl-Sepharose™ elution was subjected to conventional N-terminal protein sequencing to give the sequence in Table 5.

EXAMPLE 2

In vitro Assays of Antifungal Activity and Synergy

Antifungal activity of protein extracts and fractions was assayed by inhibition of hyphal extension of *Trichoderma reesei* on agar plates. These assays were performed as described in Roberts and Selitrennikoff, 1986 (supra) in 100×15 mm petri plates containing 10 ml of carrot juice agar medium. Five 0.25 inch diameter sterile blank paper discs were placed firmly on the agar, one in the center of a plate and four others at a distance of 1.2 cm around the central disc. Samples to be tested for antifungal activity were diluted in buffered saline, 130 mM NaCl/10 mM sodium phosphate (pH 7.4), and 25 l portions were added to each of the 4 peripheral discs. Control plates were prepared by addition of 25 l of buffered saline to each of the peripheral discs. The concentration of AFP or SAFP fractions added to discs was measured in g total protein of the fraction. Conidia from *T. reesei*, for example ATCC culture 13631, grown on a suitable agar medium were suspended in 1 ml of buffered saline, agitated vigorously to form a slightly turbid suspension and 25 l of the suspension was added to the central disc of assay and control plates. Plates were incubated at 23° C. for approximately 72 h until mycelial growth from the central disc had enveloped peripheral discs of the control plates. The formation of crescents of inhibition around sample discs indicated that the sample contained effective concentrations of antifungal agent. Inhibition assays using *Neurospora crassa* (for example, 74-OR8-1a, Fungal Genetic Stock Center, Humboldt State College, Arcata, Calif.), *Phycomyces blakesleeanus* (for example, ATCC No. 8743a) and *Alternaria alternaria* (for example, ATCC No. 16086) were performed in a similar manner except that growth conditions of the fungi were altered appropriately and Phycomyces was assayed on potato-dextrose agar medium. All of the grain AFPs acting alone exhibited antifungal activity toward Trichoderma, Phycomyces, and Alternaria. Wheat and barley AFPs did not inhibit growth of Neurospora.

Inhibition assays of *Candida albicans* and other yeasts, including Saccharomyces and Rhodotorula, were performed using a modified disc assay in which the organism was suspended in carrot juice agar medium and potential inhibitors were added to blank paper discs which were placed on the agar surface. *Candida albicans* cultures, for example, strain B-311 (ATCC 32354), were prepared by inoculating 5 ml of sterile liquid medium (1% glucose, 0.5% yeast extract) with a loopful of Candida and incubating the culture overnight at 37° C. without shaking. Candida suspension plates were prepared by adding 1 ml of the overnight culture of Candida to 100 ml of liquid carrot juice agar at 45° C., mixing and dispensing 10 ml of the agar into petri plates. After the Candida agar suspensions had solidified, five blank paper discs were placed as described above on each plate. Sample and control solutions (30 1) were added to discs. Plates were incubated at 37° C. overnight and examined for zones of growth inhibition.

In plate assays, fungal inhibition was quantified by measuring the highest dilution (i.e., lowest total protein concentration) of a sample that caused a detectable zone of inhibition around an assay disc. None of the grain SAFPs alone inhibited growth of Candida, Saccharomyces or Rhodotorula in agar plate assays. Inhibition of Candida and Rhodotorula in plate assays was observed only when SAFPs were assayed in the presence of sub-inhibitory concentrations of antifungal antibiotics, especially nikkomycin.

Antibiotic synergy plate essays were used to assay for SAFP activity. Inhibition by known antifungal antibiotics alone was assayed on plates and quantified, as described above, by adding 30 l of a buffered saline solution of known concentration of antibiotic to each assay disc. In inhibition plate assays, the approximate MIC (minimum inhibitory concentration) of an antibiotic was defined as the lowest concentration that caused a detectable zone of growth inhibition. Synergy of inhibition of known antifungal antibiotics by protein fractions, extracts or solutions was initially assayed by adding 30 l of a 1:1 admixture of antibiotic solution and protein solution to assay discs. Synergy was quantified by comparison of the MIC of the antibiotic alone to the MIC of the antibiotic/protein composition. Since none of the AFPs or SAFPs alone inhibits growth of $C.$ $albicans$ on plates, under the assay conditions employed any decrease in antibiotic MIC was scored as synergy. A synergy ratio (antibiotic MIC/antibiotic/protein combination MIC) can be employed for comparisons.

Synergy of inhibition of Candida with nikkomycin in particular, was also assessed using a slight modification of the agar plate disc method described above. A sub-inhibitory level of nikkomycin was added to liquid agar suspensions of $C.$ $albicans$ at 45° C. prior to plating. In a standard assay the final concentration of nikkomycin in the agar was about 0.2 g/ml (about 20-fold lower than the concentration of nikkomycin that alone inhibited the growth of $C.$ $albicans$). Varying concentrations of proteins to be tested for synergy were then applied to discs placed on the plates. Synergy was assessed by observation of zones of growth inhibition associated with discs.

Liquid culture assays were also employed to assess antifungal and synergistic antifungal activity of SAFP, particularly against $Candida$ $albicans$. Liquid culture assays were performed by inoculating the organism into wells of a 96-well tissue culture plate containing 150 l of fungal growth in each well. Varying concentrations of nikkomycin, SAFP and mixtures of the two agents were introduced into the wells. Plates were incubated in static culture at 37° C. for 24 hours, and wells were then examined visually for culture turbidity. Results of an experiment assessing zeamatin/nikkomycin activity against $C.$ $albicans$ are shown in Table 3, where growth was scored as +++, ++, + or no growth (–). In this experiment, the initial $C.$ $albicans$ inoculum resulted in an absorbance reading (650 nm) of about 0.005. The fungal medium employed in this experiment was 2% carrot juice medium.

A fungal growth medium low in salts, devised to promote SAFP activity and yet provide adequate nutrients to permit good fundal growth, was also employed in suspension culture assays of antifungal activity. This medium contained 0.05% glucose, 10% of the recommended concentration of MEM amino acids (Flow Laboratories) used to prepare tissue culture medium, and 10% of the fungal concentration of salts used by Vogel (1964) American Naturalist 98:435–446 to prepare fundal test medium N. $T.$ $reesei$ or $N.$ $crassa$ spores or $C.$ $albicans$ yeast cells were suspended in this medium at a concentration of approximately $1\times10^3$ organisms/ml. Portions (0.5 ml) of the fungal suspensions were added to wells of a tissue culture plate, various additions of protein and/or antibiotic were then added and the plates were incubated at 37° C. for 24 hours. Growth inhibition was defined as no visible growth at the end of this period.

Nikkomycin alone inhibited growth of $C.$ $albicans$ in liquid culture at concentrations greater than 5 g/mi. Zeamatin alone was also found to inhibit growth of $C.$ $albicans$ in liquid culture. This result was surprising in light of disc diffusion assays on agar which showed no $C.$ $albicans$ growth inhibition with zeamatin alone. The reason for these differing results is not known. In any event, zeamatin displays synergizing activity with nikkomycin in liquid assays. The MIC of nikkomycin was reduced from about 17 to about 0.17 g/ml by the addition of 0.3 g/ml of zeamatin. The zeamatin employed in these experiments was that purified by phenyl-Sepharose™ chromatography (peak 2, FIG. 3).

A bioautography procedure was developed to assess the presence of anti-Candida synergy activity in protein bands separated on non-reducing SDS-PAGE. This procedure allowed the specific association of SAFP activity with a separated protein band on a gel. Protein samples to be tested in the bioautography technique were added to non-reducing Laemmli sample buffer (final concentration 15% sucrose, 2.5% SDS, 125 mM Tris-HCl, PH 6.7) and boiled for 5 minutes prior to running on a 12% polyacrylamide gel. Gels were then incubated inelution buffer containing 1% Triton-X100 for 2 hours at 37° C. to remove SDS. After being washed well in water, the gels were incubated in 2% carrot juice medium (or other desired growth medium) for 10 minutes. The gels were then placed in 150 mm diameter petri dishes over which an agar solution (1.5% agar in 2% carrot juice medium or other desired fungal growth medium) containing a sub-inhibitory level of nikkomycin (0.2 g/ml and $C.$ $albicans$ (1 ml of an overnight culture to 100 ml of agar solution) was poured and allowed to solidify. After overnight incubation at 37° C., the position of SAFP's can be seen as a clear band (no growth) against a background of Candida growth. Alternatively, the washed protein gels can simply be placed on a $Candida$ $albicans$ suspension plate containing a sub-inhibitory level of nikkomycin and allowed to incubate. Proteins diffuse from the gel into the agar to produce a clear zone of growth inhibition that is associated with the protein band. These assays can be employed with purified protein fractions, partially purified protein fractions or crude protein extracts.

Protein extracts, fractions and solutions were quantified for total protein/ml using the Bradford dye-binding method.

Carrot juice medium was prepared by first autoclaving 20 g of carrot slices in 180 ml water. The resulting carrot juice was then diluted 1:9 (v/v) with water, agar (2% w/v) was added and the mixture was again autoclaved. Assays were also performed using a richer nutrient broth agar medium (infra).

Partially purified nikkomycin, which is a combination of nikkomycin X and Z, approximately 70% pure, was obtained as a gift from Bayer A.-G. A formulation that includes nikkomycin X and Z is believed to be commercially available in Europe as an agricultural fungicide. Nikkomycin Z and nikkomycin X can be purified from this mixture by known methods (Zahner et al. (1981 ) U.S. Pat. No. 4,287,186). Nikkomycin Z is also commercially available (Calbiochem, San Diego, Calif., Cat. No. 481995). Amphotericin B was obtained from commercial sources (Sigma, St. Louis, Mo.) and papulacandin B, approximately 80% pure, was a gift from Ciba-Geigy Corp. (Basel, Switzerland). Polyoxin B was purified from polyoxin AL wettable powder as described in Selitrennikoff (1982) Neurospora Newsletter, no. 29, p. 27.

EXAMPLE 3

Chemical and Biological Properties of Zeamatin

The grain SAFPs are all highly basic proteins as evidenced by their strong binding to CM-Sephadex™.

Zeamatin partially purified by CM-Sephadex™ (fraction CMS) displayed both chitinase and β-1, 3 glucanase activity in addition to antifungal activity against *T. reesi* and *N. crassa*, and synergistic activity in combination with antifungalantibiotics, especially nikkomycin, against *Candida albicans*. Phenyl-Sepharose™-purified zeamatin displayed no chitinase, mannanase or β-N-acetylhexosaminidase activity, and little or no glucanase activity. Synergistic antifungal activity is not associated with the presence of chitinase or glucanase activity.

Chitinase, β-1,3 glucanase, β-1,6 glucanase, mannanase and β-N-acetylhexosaminidase activities were assayed by measuring the increase of reducing sugar, analogous to the procedure of Dubois et al. (1956) Anal. Chem. 28:350–356. RIP activity of proteins was assessed as described in Coleman and Roberts (1982), supra, by adding dilutions of the protein to be assayed to extracts from Ehrlich ascites cells or *N. crassa* cells, incubating the cell-free reaction mixes with labelled amino acids, and measuring any protein-induced decrease in incorporation of label into acid insoluble material (i.e., newly synthesized protein).

Trypsin inhibition of proteins was assessed as inhibition of trypsin degradation of the chromogenic trypsin reagent BAPNA (N-α-benzoyl-DL-arginine-p-nitroanilide). Specifically, varying amounts of proteins to be assayed were added to 0.1 ml of trypsin solution (40 g/ml in pH 8.0 Tris buffer). The solutions were incubated at room temperature for 10 minutes, after which 1.0 ml of BAPNA (0.4 mg/ml) was added to each. The reactions were then incubated at 370° C. for an additional 10 minutes and assayed for production of a yellow color (410 nm). Soybean trypsin inhibitor was employed as a positive control (i.e., no yellow color was produced in the presence of 10 g soybean trypsin inhibitor). In the case of zeamatin, addition of 150 g of purified zeamatin had no effect on trypsin activity in the assays described.

EXAMPLE 4

Comparison of zeamatin/nikkomycin anti-Candida synergy on different growth media Synergy assays were performed as described above with Candida, except that assays were also performed on a rich nutrient broth agar medium. Nutrient agar assay plates were prepared as above, substituting a commercial nutrient agar medium for carrot juice agar. Incubation times were modified appropriately.

In the growth medium comparison, relative inhibition by nikkomycin Z and zeamatin/nikkomycin Z mixtures was assayed. In zeamatin/nikkomycin Z mixtures, an excess of zeamatin (15 g protein) as fraction CMS was added to each assay disc and the concentration of nikkomycin Z was varied. The MIC of nikkomycin Z in the presence and absence of zeamatin was determined as the lowest concentration of the antibiotic that affects measurable growth inhibition of *Candida albicans*. As shown in Table 4, the MIC of nikkomycin Z against *C. albicans* grown on nutrient agar was found to be about 9 fold higher than the MIC against *C. albicans* grown on the less-rich carrot juice medium. It is believed that the higher MIC on rich medium is due to the presence of inhibitory levels of peptides in the medium. Zeamatin was found to lower the MIC of Nikkomycin Z on both rich and poor media. Interestingly, in most cases the nikkomycin Z MIC was lowered about 100 fold in the presence of zeamatin on both media. The minimum amount of partially purified zeamatin (fraction CMS) required to synergize with nikkomycin Z (25 ng/disc or about 0.8 g/ml) was approximately 0.3 g protein per disc (about 10 g/ml) for assays carried out in both rich and poor media.

EXAMPLE 5

Relative sensitivity of *Candida albicans* strains to zeamatin/nikkomycin compositions Several recent clinical isolates of *Candida albicans* were obtained from Dr. B. Reller, Department of Medicine, University Hospital, Denver, Co. The sensitivity of the clinical isolates to the synergistic zeamatin/nikkomycin composition was assayed and compared to that of the laboratory isolate used in the initial assays. Assays were performed as described above, employing nikkomycin Z (Calbiochem) and purified zeamatin. Assays were done on carrot juice agar as well as on nutrient broth agar plates. The results are presented in Table 4. Nikkomycin Z MIC's were determined alone and in the presence of an excess of zeamatin (15 g protein/disc) provided as fraction CMS. There was wide variation in strain sensitivity to both nikkomycin Z alone and zeamatin/nikkomycin Z mixtures. In all cases, the MIC of nikkomycin was lowered in the presence of zeamatin, and synergy was about as effective on poor medium as on rich medium.

EXAMPLE 6

Isolation and Purification of Sormatin from Sorghum

Sormatin was isolated and purified from sorghum following a procedure similar to that used in the isolation and purification of zeamatin from corn. Specifically, Pioneer Hi-Bred #8333 sorghum was ground finely in a coffee grinder. Sorghum meal was extracted for 1 h at 4° C. with a buffer containing 50 mM NaCl, 25 mM NaPO$_4$, 5 Mm EDTA (pH 7.4). The resulting suspension was centrifuged (10,000× g, 20 min, 4° C.) and the supernatant protein extract was saved.

Figure 5:
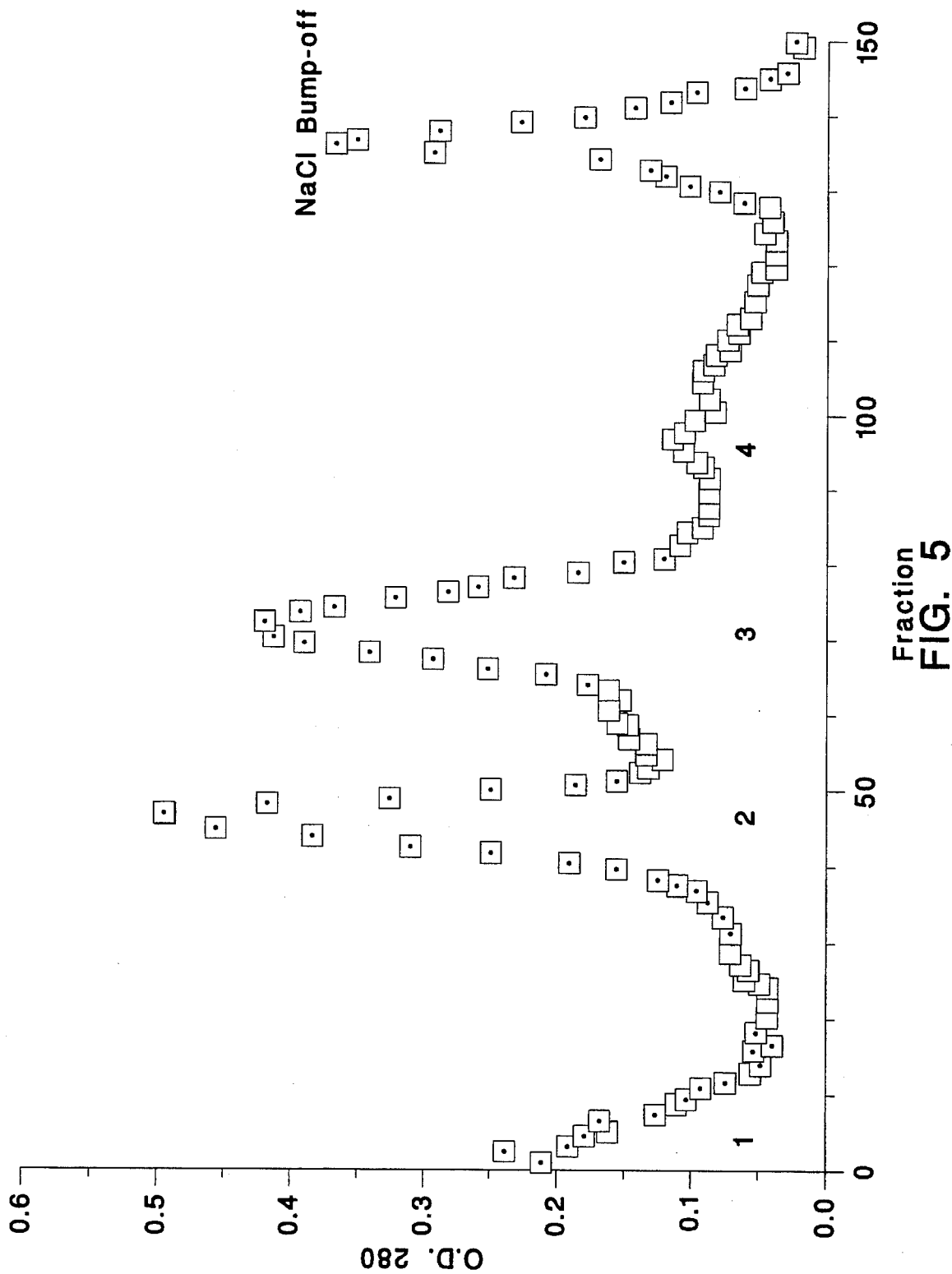
FIG. 5 is an elution profile from the initial CM-Sephadex™ column purification step of SAFP from sorghum protein extracts. Protein in each fraction was quantified by measurement of absorbance at 280 nm. Bound protein was eluted with a linear salt gradient (0.0 1–0.4 m NaCl). Four peaks were eluted. Nikkomycin Z synergy was assayed on *C. albicans* suspension plates (carrot juice agar medium) by adding 30 l of a 1:10 dilution of each column fraction with 25 mg of antibiotic to assay discs. Only the third peak contained synergistic activity. Peak 3 was concentrated using Amicon YM-10 filter.
Figure 6:
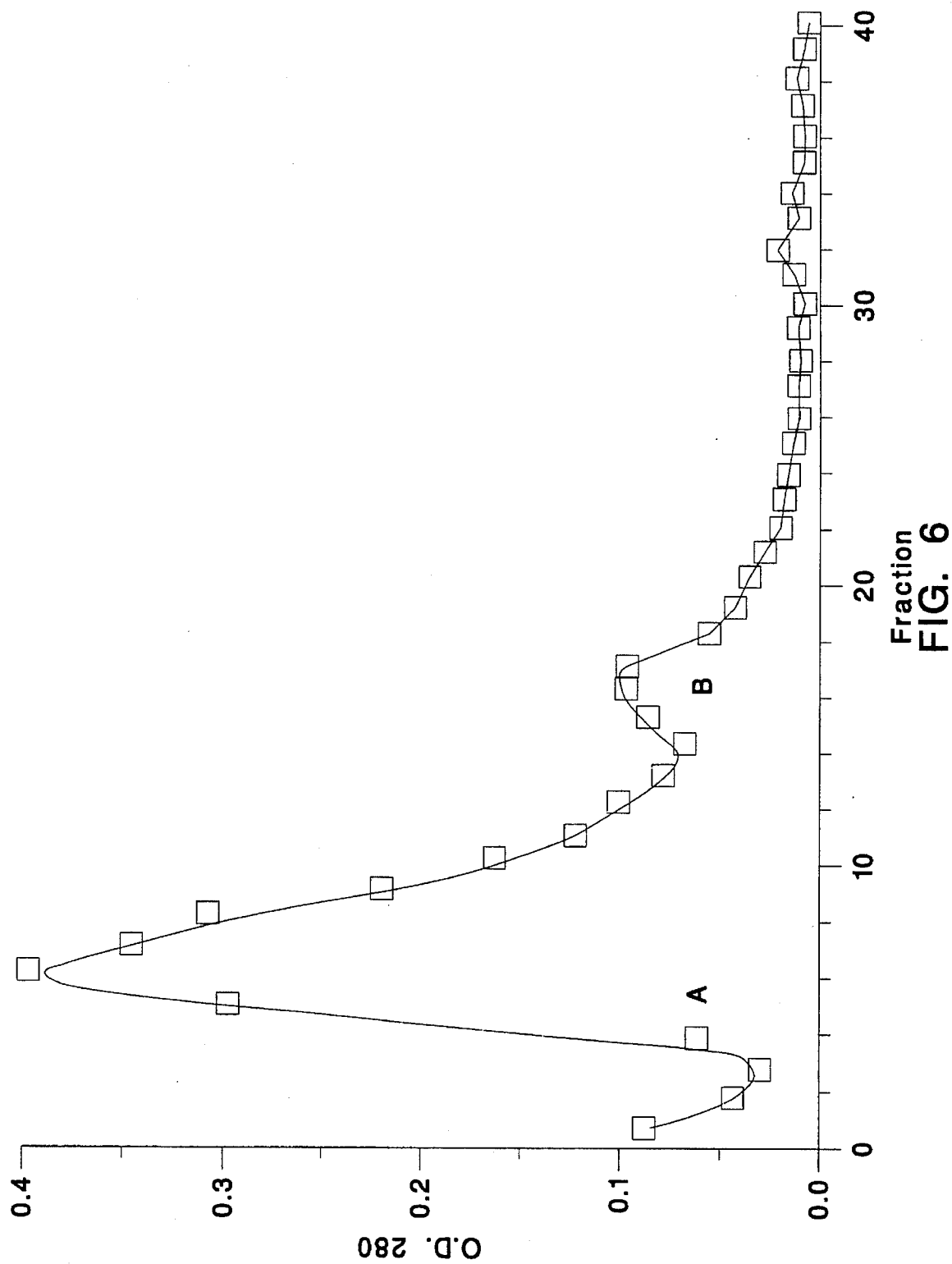
FIG. 6 is an elution profile of phenyl-Sepharose™ column chromatograph purification of sormatin. Peak 3 (FIG. 5) was loaded onto a pre-equilibrated column comprising 1M NaCl, 0.005M sodium phosphate, 0.001M EDTA, pH 7.4. The column was washed with 10 ml of the above buffer, then eluted with a linear salt gradient (0.01–0.4M NaCl). Protein was quantified by measurement of absorbance at 280 nm. Only peak B contained synergistic activity.
Figure 7:
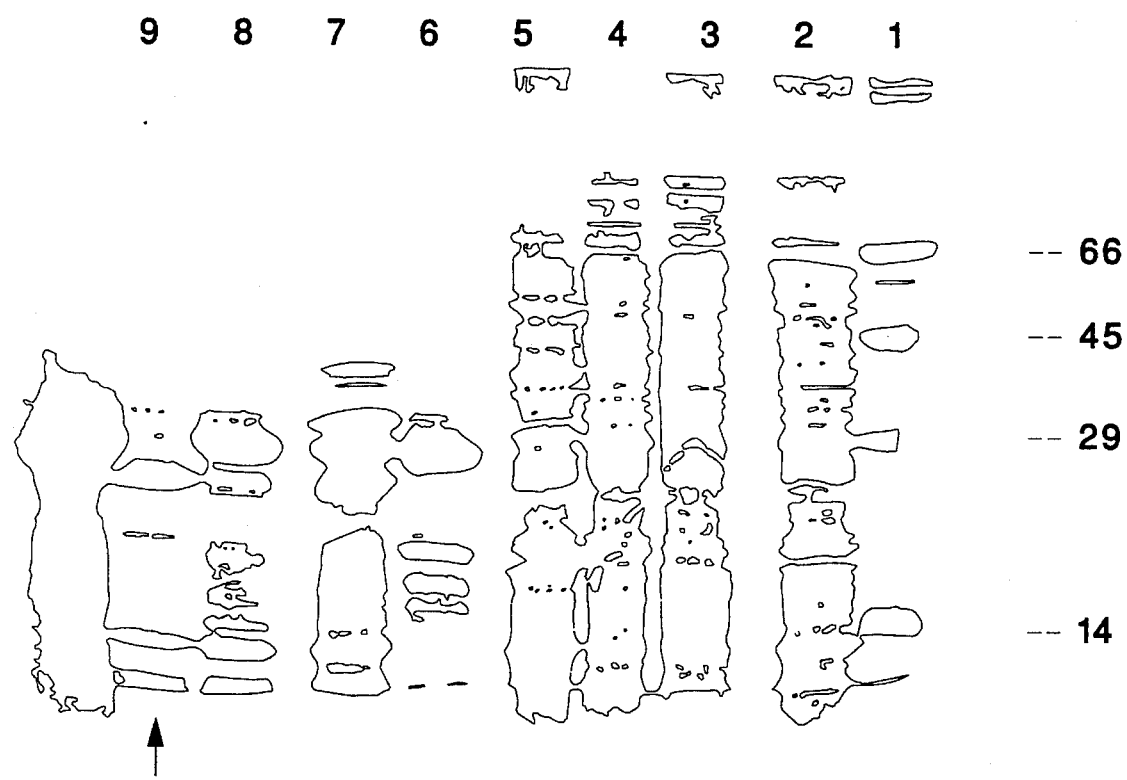
FIG. 7 is a photograph of an SDS-polyacrylamide gel electrophoresis run under reducing conditions of various protein fractions from the CM-Sephadex™ separation (FIG. 5) and phenyl-Sepharose™ separation (FIG. 6) or sorghum extract. Lanes 1–5 contain molecular weight standards as indicated, crude extract, 0–35%, 35–65%, and 65–100% ammonium sulfate cuts, respectively. Lanes 6 and 7 contain Peaks 2 and 3 (FIG. 5) from the CM-Sephadex™ separation, respectively. Lanes 8 and 9 contain Peaks A and B (FIG. 6) from the phenyl-Sepharose™ separation, respectively.

Ammonium sulfate was slowly added with stirring to the sorghum protein extract, to obtain a 35% sainted solution which was left overnight at 4° C. The solution was then centrifuged (10,000× g, 30 min, 4° C.), the pellet discarded and the supernatant was made 65% saturated with ammonium sulfate. The solution was left 20 min at 4° C., centrifuged (10,000× g, 30 min, 4° C.) and the supernatant was discarded. The remaining protein pellet was resuspended in buffer containing 10 mM NaCl, 5 mM NaPO$_4$, 1 mM EDTA (PH 7.4) and dialyzed for about 18 h at 4° C. with four changes of the same resuspension buffer. The dialyzed solution was clarified by centrifugation (10,000× g, 20 min, 4° C.). A CM-Sephadex™ column (about 60 ml of packed gel volume) was equilibrated with resuspension buffer. The dialyzed solution was loaded onto the column; the column was then washed with buffer until the absorbance of the effluent at 280 nm had fallen to about 0.2. A linear NaCl gradient (resuspension buffer (pH 7.4) plus NaCl) from 10 nM NaCl gradient (resuspension buffer (pH 7.4) plus NaCl) from 10 mM NaCl to 400 mM NaCl was applied to the column as described in Example 1 employing the slower flow rate of about 1 m /min. FIG. 5 shows the elution profile from the CM-Sephadex™ column purification of sormatin comprising four peaks. The fractions comprising peak III were concentrated using an Amicon YM-10 filter and the concentrate was loaded on a phenyl-Sepharose™ (CL-4B) column. Phenyl-Sepharose™ chromatography was carried out as described in Example 1 for zeamatin. The sample was loaded onto the column at a low salt concentration employing 0.1M NaCl. The elution profile is shown in FIG. 6. Only peak B contained synergistic anti-Candida activity. FIG. 7 shows SDS-polyacrylamide gel electrophoresis under reducing conditions of crude sorghum extract and various protein fractions. Lane 9 is the phenyl-Sepharose™ peak B fraction containing the approximately 25 kd sorghum protein having synergistic antifungal activity. Sormatin is believed to be about 70–80% pure after phenyl-Sepharose™ chromatography.

The protein material isolated from peak B, sormatin, was subjected to conventional N-terminal protein sequencing techniques to obtain the sequence given in Table 5.

Sormatin, either in purified or partially purified form, has synergistic antifungal activity similar to that of zeamatin.

EXAMPLE 9

Protein Sequence Determination of Zeamatin

Example 1 describes the purification of zeamatin and the determination of the aminoterminal sequence of the zeamatin protein (see table 5). In addition, purified zeamatin and chymotryptic digestion products were subjected to amino acid sequence determination using techniques known in the art. The protein sequence was found to be identical to the sequence published by Richardson et al. and from the Richardson sequence the entire 206 amino acid sequence can be predicted. This is shown in table 6. Underlined sequences are those determined from chymotryptic digestion products. The mature protein starts on an alanine as a 21 amino acid signal sequence is removed from the pre-protein.

TABLE 6

Amino Acid Sequence of Zeamatin (SEQ ID NO: 3)

| | |
|---|---|
| 1 | AVFTVVNQCPFTVWAASVPVGGGROLNRGESWRITAPAGTTAARIWARTG |
| 51 | CQFDASGRGSCRTGDCGGVVQCTGYGRAPNTLAEYALKQFNNLDFFDISI |
| 101 | LDGFNVPYSFLPDGGSGCSRGPRCAVDVNARCPAELRQDGVCNNACPVFK |
| 151 | KDEYCCVGSAANNCHPTNYSRYFKGQCPDAYSYPKDDATSTFCPAGTNY |
| 201 | KVVFCP |

EXAMPLE 7

Isolation and Partial Purification of SAFP from Oats

Avematin from oat meal was isolated and purified to the CM-Sephadex™ step as described above for zeamatin employing the same buffer extraction procedure (buffer pH

EXAMPLE 10

Cloning of a Zeamatin cDNA

Based on the complete amino acid sequence of zeamatin (see example 9) the following degenerate oligonucleotides were designed:

| | |
|---|---|
| SP86 | ATGTGAATTCGGICAIAAIACYTTRTARTT (SEQ ID NO: 4) |
| SP87 | ATGTGAATTCAICAITAYTCITCYTTYTTIAA (SEQ ID NO: 5) |
| SP88 | GTACGGATCCAAYCAITGYCCITTYACIGTITGG (SEQ ID NO: 6) |

Figure 9:
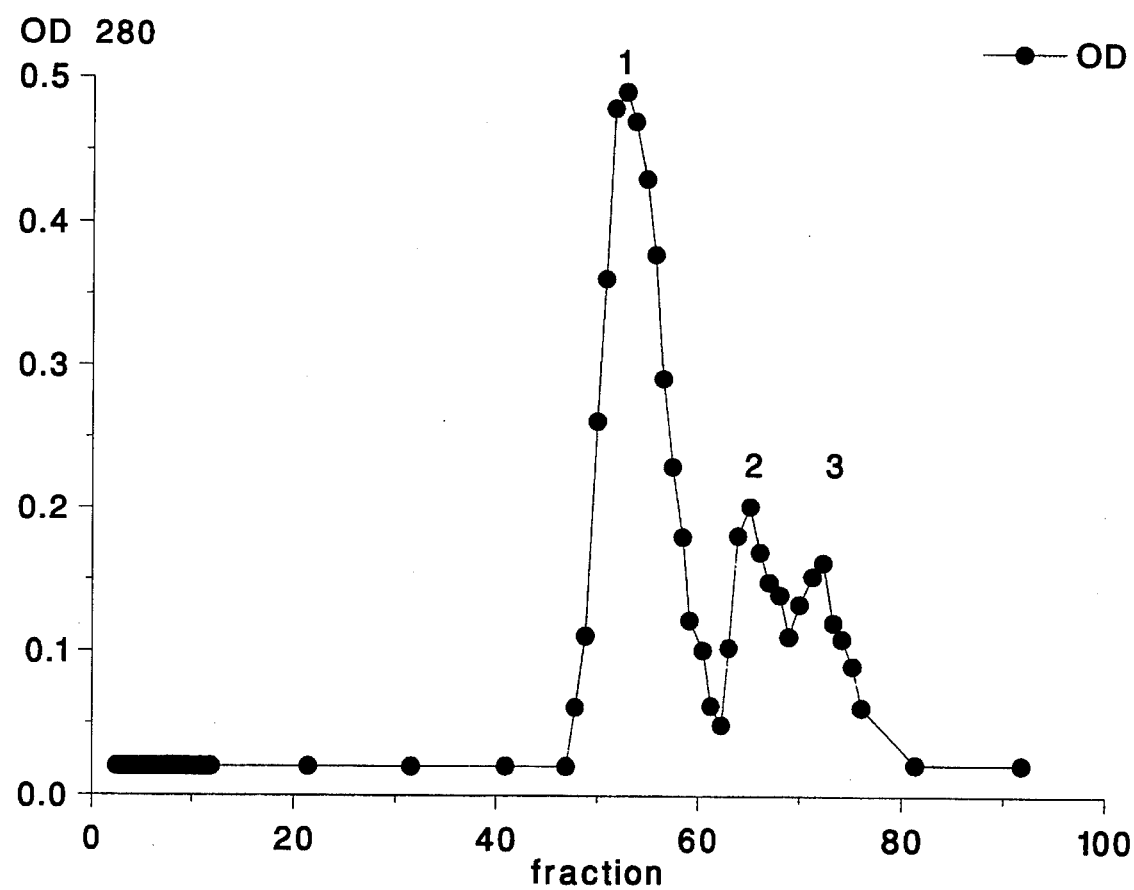
FIG. 9 is the CM-Sephadex elution profile of avematin activity. Elution is performed as described in Example 7. Three peaks were eluted in the separation. Only peak I was found to contain synergistic antifungal activity.
Figure 10:
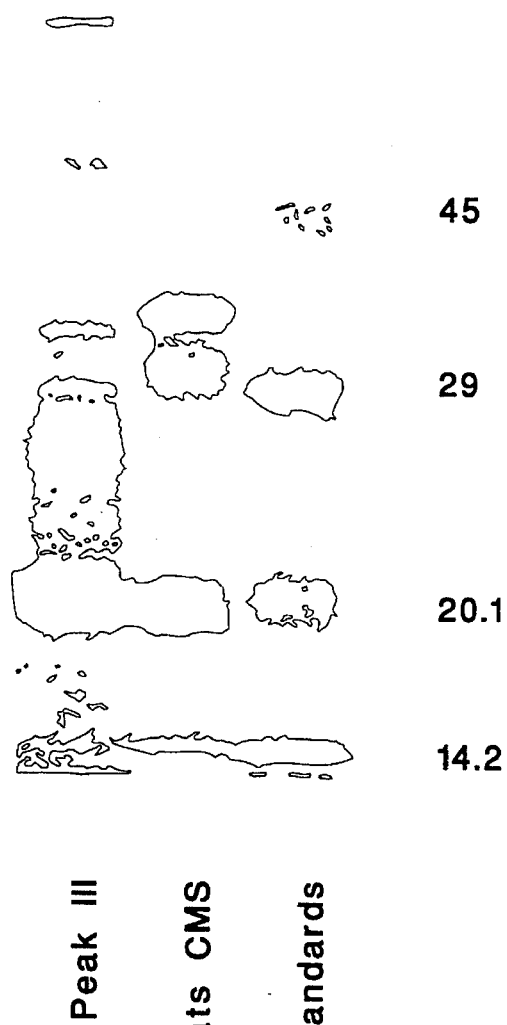
FIG. 10 is a photograph of an SDS-gel electrophoresis run under reducing conditions containing the CM-Sephadex peak I from the oat-SAFP purification in FIG. 9. Lane 1 contains molecular weight standards as indicated. Lane 2 is the avematin CM-Sephadex peak I and Lane 3 contains peak 3 of the CM-Sephadex separation of corn extract containing zeamatin.

7.0) and ammonium sulfate fractionation. CM-Sephadex™ chromatography was performed using a linear salt gradient (10 mM NaCl-400 mM NaCl) employing 1 ml/min flow rate to give the CM-Sephadex™ elution profile given in FIG. 9. Peak I of FIG. 9 was found to contain synergistic antifungal activity, particularly anti-Candida activity. FIG. 10 shows the results of SDS polyacrylamide gel electrophoresis under reducing conditions of peak I of FIG. 9. Avematin is believed to be about 50% pure when purified by this CM-Sephadex™ procedure.

Avematin in partially purified form has synergistic antifungal activity and antifungal activity similar to zeamatin.

EXAMPLE 8

SAFP Activity In Non-Grain Plant Extracts

As described above, SAFP activity has been detected in crude and partially purified extracts of a variety of grains. Using in vitro synergy assays as described in Example 2, extracts of other plants can be assessed for the presence of SAFP activity. For example, SAFP activity has been detected in extracts of soybeans. Soybeans were ground and extracted with buffer (50 mM NaCl, 20 mM NaPO$_4$ buffer, 5 mM EDTA, pH 7.4) and the extract clarified by centrifugation (10,000× g, 20 m, 4° C.). The crude extract was found to synergize with nikkomycin against C. albicans in in vitro plate assays. Thus, SAFP activity is not limited to grains and is likely to be found in a variety of other plant seeds and other plant materials.

From the amino acid sequence SP86 and SP88 would predictably amplify a DNA fragment of 600 bp, and SP87 and SP88 a fragment of 450 bp from the zeamatin cDNA. Oligonucleotides SP86 and SP87 included an EcoRI site at their 5' terminus and oligonucleotide SP88 included a BamHI site at its 5' terminus. These restriction sites are for the purposes of facilitating the cloning of the PCR fragments generated. Note that Y=pyrimidine, R=purine, and I=inosine.

First strand cDNA was synthesized from polyA+RNA from 6 day-old light-grown maize shoots and used as a template in the polymerase chain reaction using 40 cycles of 94° C./1 min., 50° C./1.5 min., 72° C./1.5 min. Both oligonucleotides generated fragments of the predicted size, which were gel-purified and reamplified. The fragments were subsequently cloned into pBluescript and sequence determination of the resultant plasmids confirmed that the correct zeamatin sequence had been amplified.

Probes generated from the zeamatin cloned sequences were radio-labelled and used to screen a cDNA library (in λZiplox) from 7-day old maize B73. Three separate full-length cDNA clones were isolated and, following in vivo excision, the DNA sequence of each was determined. All three clones were found to be identical in sequence. The full-length zeamatin cDNA is presented in Table 7.

TABLE 7 cDNA Sequence of Zeamatin (SEQ ID NO: 7)

|   |   |   |   |   |   |
|---|---|---|---|---|---|
| 1 | TTCAAATACT | TGCATAAG<u>AT</u> | <u>G</u>GCAGGTTCC | GTGGCAATCG | TGGGCATCTT |
| 51 | CGTCGCCCTC | CTCGCCGTGG | CCGGCGAGGC | GG<u>CT</u>GTGTTC | ACGGTGGTGA |
| 101 | ACCAGTGCCC | GTTCACCGTG | TGGGCCGCGT | CCGTGCCGGT | GGGCGGCGGG |
| 151 | CGGCAGCTGA | ACCGCGGCGA | GAGCTGGCGG | ATCACGGCCC | CCGCGGGCAC |
| 201 | GACGGCCGCG | CGCATCTGGG | CGCGCACGGG | GTGCAAGTTC | GACGCGAGCG |
| 251 | GGCGCGGGAG | CTGCCGCACG | GGGGACTGCG | GCGGCGTGCT | GCAGTGCACT |
| 301 | GGGTACGGGC | GCGCGCCCAA | CACGCTGGCG | GAGTACGCTC | TGAAGCAGTT |
| 351 | CACAACCTCG | ACTTCTTCGA | CATCTCCCTC | ATCGACGGCT | TCAACGTGCC |
| 401 | CATGAGCTTC | CTCCCCGACG | GCGGGTCCGG | GTGCAACCGC | GGCCCGCGCT |
| 451 | GCGCCGTGGA | CGTGAACGCG | CGCTGCCCTG | CCGAGCTGCG | GCAGGACGGC |
| 501 | GTGTGCAACA | ACGCGTGCCC | CGTGTTCAAG | AAGGACGAGT | ACTGCTGCGT |
| 551 | CGGCTCGGCG | GCCAACGACT | GCCACCCGAC | CAACTACTCC | AGGTACTTCA |
| 601 | AGGGGCAGTG | CCCCGACGCG | TACAGCTACC | CCAAGGATGA | CGCCACCAGC |
| 651 | ACCTTCACCT | GCCCCGCCGG | AACCAACTAC | AAGGTCGTCT | TCTGCCCGTG |
| 701 | AGGCCGCTGA | ACTAGCATCA | GCGTGCGCGC | GTCGACCAAG | AACAAGAAAT |
| 751 | AAACGACCGA | GGCTGTGTAT | GTTGCCCGCC | GTGTGCTCAA | CTGGAGCAAA |
| 801 | AATAAAGCCA | ACAAAACAAG | CACGTGTGAT | CTCTATGTCA | CCAACTCTAT |
| 851 | CACCTTAATT | AATGGGGCAT | TATGAAAAAA | AAAAAAAAAA | AAAA |

The ATG codon for the first methionine and the first codon of the mature peptide are underlined.

EXAMPLE 11

Expression of the Zeamatin cDNA in Transgenic Plants

The cDNA for zeamatin was expressed behind the constitutive 35S promoter in transgenic plants. The 913 bp cDNA was transferred as an EcoRI-NotI fragment from pBluescript to the vector pCGN1761/ENX which carries the double 35S CaMV promoter and the tml transcriptional terminator on a pUC-derived plasmid. Colonies carrying the cDNA in sense were recovered and named pZMT-A. The expression cassette of pZMT-A was subsequently excised as an XbaI fragment and cloned into pCIB200 and colonies oriented in such a way that the 35S promoter was located adjacent to the selectable marker were used in plant transformations using Agrobacterium. For direct gene transfer, the pZMT-A expression cassette is transferred as a HindIII-BamHI fragment to the vector pCIB3064. Transformation to transgenic plants is undertaken using techniques well known in the art. For transformation of dicotyledonous species using binary Agrobacterium vectors such as pCIB200 see Alexander et al. (PNAS in press), and for transformation of monocotyledonous species using direct gene transfer vectors such as pCIB3064 see Koziel et al. (1993; Biotechnology 11: 194–200). Transgenic plants are screened for high-level expression of the zeamatin cDNA using antibodies which recognize the zeamatin protein or by Northern analysis. Plants which express high levels of the zeamatin protein are found to have enhanced resistance to plant pathogens.

Other promoters are suitable for the expression of zeamatin in transgenic plants. These include (but are not restricted to) constitutive promoters (such as those from the ubiquitin and actin genes), cell and tissue-specific promoters (examples), and promoters which are expressed upon wound induction, infection or upon initiation of the plant response to infection (such as the tobacco PR1 promoter).

Other synergistic antifungal protein cDNAs can be expressed in trangenic plants in a manner analogous to that described for zeamatin in example 11.

We claim:
1. An isolated DNA sequence comprising the DNA sequence set forth in SEQ ID NO: 7.

2. A vector comprising the DNA sequence of claim 1.

* * * * *